US006469177B1

(12) United States Patent
Worley et al.

(10) Patent No.: US 6,469,177 B1
(45) Date of Patent: Oct. 22, 2002

(54) SURFACE ACTIVE N-HALAMINE COMPOUNDS

(75) Inventors: Shelby D. Worley, Auburn, AL (US); Michael W. Eknoian, Warren, NJ (US); Yanjun Li, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 09/710,090

(22) Filed: Nov. 10, 2000

Related U.S. Application Data

(60) Continuation-in-part of application No. 09/246,217, filed on Feb. 8, 1999, now Pat. No. 6,162,452, which is a division of application No. 09/987,698, filed on Dec. 9, 1997, now Pat. No. 5,902,818.

(51) Int. Cl.$^7$ ............................................. C07D 233/22
(52) U.S. Cl. .................................................... 548/333.5
(58) Field of Search ...................................... 548/333.5

(56) References Cited

U.S. PATENT DOCUMENTS

| | | |
|---|---|---|
| 2,225,384 A | 12/1940 | Graenacher et al. |
| 3,519,608 A | 7/1970 | Kelley et al. |
| 3,931,213 A | 1/1976 | Kaminski et al. |
| 4,000,293 A | 12/1976 | Kaminski et al. |
| 4,349,646 A | 9/1982 | Nudel et al. |
| 4,420,590 A | 12/1983 | Gartner |
| 4,681,948 A | 7/1987 | Worley |
| 4,767,542 A | 8/1988 | Worley et al. |
| 4,955,392 A | 9/1990 | Sorkin |
| 5,126,057 A | 6/1992 | Worley et al. |
| 5,284,157 A | 2/1994 | Miller et al. |
| 5,338,859 A | 8/1994 | Bhattacharya |
| 5,490,983 A | 2/1996 | Worley et al. |
| 5,670,646 A | 9/1997 | Worley et al. |
| 5,756,764 A | 5/1998 | Fenteany et al. |
| 5,882,357 A | 3/1999 | Sun et al. |
| 5,981,668 A | 11/1999 | Fujita et al. |

OTHER PUBLICATIONS

Chemical Abstract No. 40044 (1968).
Chemical Abstract No. 444909 (1970).
Williams, D.E. et al., "Is Free Halogen Necessary for Disinfection?," *Applied and Environmental Microbiology*, vol. 54, No. 10, Oct. 1988, pp. 2583–2585.
Hazziza–Laskar, J., et al., "Biocidal Polymers Active by Contact. I. Synthesis of Polybutadiene with Pendant Quaternary Ammonium Groups," *Journal of Applied Polymer Science*, vol. 50, No. 4, Oct. 20, 1993, pp. 651–662.
Hazziza–Laskar, J., et al., "Biocidal Polymers Active by Contact. IV. Polyurethanes Based on Polysiloxanes with Pendant Primary Alcohols and Quaternary Ammonium Groups," *Journal of Applied Polymer Science*, vol. 58, No. 1, Oct. 3, 1995, pp. 77–84.

Nurdin, N., et al., "Biocidal Polymers Active by Contact. II. Biological Evaluation of Polyurethane Coatings with Pendant Quaternary Ammonium Salts," *Journal of Applied Polymer Science*, vol. 50 (1993) p. 663–670.
Nurdin, N., et al. "Biocidal Polymers Active by Contact. III. Ageing of Biocidal Polyurethane Coatings in Water," *Journal of Applied Polymer Science*, vol. 50 (1993) pp. 671–678.
Kanazawa, A., et al., "Polymeric Phosphonium Salts as a Novel Class of Cationic Biocides. III. Immobilization of Phosphonium Salts by Surface Photografting and Antibacterial Activity of the Surface–Treated Polymer Films," *Journal of Polymer Science: Part A: Polymer Chemistry*, vol. 31, No. 6, May 1993, 1467–1472.
Kanazawa, A., et al., "Polymeric Phosphonium Salts as a Novel Class of Cationic Biocides. VI. Antibacterial Activity of Fibers Surface–Treated with Phosphonium Salts Containing Trimethoxysilane Groups," *Journal of Applied Polymer Science*, vol. 52 (1994) 641–647.
Oh, S.–T., et al., "Synthesis and Fungicidal Activities of Polymeric Biocides. I. TBZ–Containing Monomer and Polymers," *Journal of Applied Polymer Science*, vol. 52, No. 5, May 2, 1994, pp. 583–589.
Oh, S.–T., et al., "Synthesis and Fungicidal Activities of Polymer. III. Bactericidal Activity of Homopolymer of AcDP and Copolymer of AcD with St," *Journal of Applied Polymer Science*, vol. 54, No. 6, Noc. 7, 1994, pp. 859–866.
Cho, W.J., et al., "Synthesis and Biocidal Activities of Polymer. II. Bactericidal Activity of Homopolymer of AcDP Copolymer of AcD with MMA," *Journal of Macromolecular Science–Pure and Applied Chemistry*, vol. A32, No. 3 (1995) pp. 479–495.
Hayes, R.A., "Polymeric Chain Transfer Reactions. Polymerization of Some Vinyl Monomers in the Presence of Vinyl Polymers," *Journal of Polymer Science*, vol. XI, No. 6, pp. 531–537 (Dec. 1953).
Dupont Advertisement, *Chemical Engineering News*, vol. 26, No. 6, Feb. 9, 1948.

(List continued on next page.)

*Primary Examiner*—T. A. Solola
*Assistant Examiner*—Joseph Murray
(74) *Attorney, Agent, or Firm*—Christensen O'Connor Johnson Kindness PLLC

(57) ABSTRACT

N-halamine biocidal materials and coatings are provided. Monomeric oxazolidinones or hydantoins are homopolymerized or copolymerized with other monomers so as to produce materials or coatings, which upon exposure to solutions of chlorine or bromine become biocidal. The biocidal materials and coatings are effective at inactivating microorganisms upon surface contact and are regenerable following loss of efficacy upon further exposure to solutions of chlorine or bromine. Surfaces which could be treated with the materials and coatings include, but are not limited to: glass, plastic, metals, fibers, and wood for use in pool and tank liners, food wrappers, catheters, paints, tiles, shower walls, fabrics, sterile bandages, pipes, medical and dental coatings, preservatives, and the like.

3 Claims, No Drawings

OTHER PUBLICATIONS

Emerson, D.W., et al., "Functionally Modified Poly(styrene-divinylbenzene). Preparation, Characterization, and Bactericidal Action," *Industrial & Engineering Chemistry Product Research and Development*, vol. 17, No. 3, Sep. 1978, pp. 269–274.

Emerson, D.W., "Slow Release of Active Chlorine and Bromine from Styrene–Divinylbenzene Copolymers Bearing N,N–Dichlorosulfonamide, N–Chloro–N–alkylsulfonamide, and N–Bromo–N–alkylsulfonamide Functional Groups. Polymer–Supported Reagents. 6," *Industrial & Engineering Chemistry Research*, vol. 30, No. 11, Nov. 1991, pp. 2426–2430.

Emerson, D.W., "Polymer–Bound Active Chlorine: Disinfection of Water in a Flow System. Polymer Supported Reagents. 5," *Industrial & Engineering Chemistry Research*, vol. 29, No. 3, Mar. 1990, pp. 448–450.

Sun, G., et al., "New Cyclic N–Halamine Biocidal Polymer," *Ing. Eng. Chem. Res.* 33:168–170, 1994.

Sun, G., et al., "Performance of a New Polymeric Water Disinfectant," *Journal of the American Water Resources Association* 32(4):793–797, Aug. 1996.

Sun, G. et al., "Preparation of Novel Biocidal N–Halamine Polymers," *Journal of Bioactive and Compatible Polymers* 10:135–144, Apr. 1995.

"Water Absorbing Composition Manufacture" (abstract) [online], *Research Disclosure* RD 434052 A, Jun. 10, 2000 [retrieved Oct. 4, 2001], retrieved from West, Derwent World Patents Index Accession No. 2000–530587.

Worley, S.D. et al., "Biocidal Polymers," *Trip* 4:11:364–370, Nov. 1996.

SURFACE ACTIVE N-HALAMINE COMPOUNDS

RELATED APPLICATIONS

This application is a continuation in part of U.S. patent application Ser. No. 09/246,217, filed Feb. 8, 1999, now U.S. Pat. No. 6,162,452 which in turn is a Divisional of U.S. patent application Ser. No. 08/987,698, filed on Dec. 9, 1997, now U.S. Pat. No. 5,902,818.

FIELD OF THE INVENTION

The following invention relates to disinfectant compounds that act as biocides to an array of microorganisms. The biocides are comprised of cyclic N-halamines that are biocidal when they come in contact with halogen-sensitive organisms for a specific contact time. This is achieved by coating the N-halamine on a substrate; such as, but not limited to: glass, metal, wood, plastic, concrete, and fabric.

BACKGROUND OF THE INVENTION

Current surface contact biocides for the use of producing a sterile environment such as for medical tables, surgical equipment, fabric materials, gloves, catheter tubing, piping, industrial and commercial surfaces, swimming pools, floors, can and bottle liners, food production equipment and liners, and various medical and dental applications do not exist or are severely limited in their biocidal abilities. Most commonly used water-soluble disinfectants which contain free halogen have severely limited lifetimes, produce adverse reactions to their environment, and produce toxic by-products. Disinfectants which do not contain free halogen, such as quaternary ammonium and phenolic compounds, are only effective towards specific organisms, are water soluble, and can cause skin and eye irritation. Commercially employed hydantoins, cyanurates, oxazolidinones (Kaminski et al., U.S. Pat. Nos. 4,000,293 and 3,931,213), imidazolidinones (Worley et al., U.S. Pat. Nos. 4,681,948; 4,767,542; 5,057,612; 5,126,057), and polymeric N-halamines (Worley et al., U.S. Pat. Nos. 5,490,983 and 5,670,646) are much more stable than free halogen, ozone, and chlorine dioxide, and are more versatile than phenolic and quaternary ammonium compounds.

Currently only a few disinfectant surfaces have been prepared, most of which focus on quaternary ammonium compounds (quats) anchored on polymer backbones (Hazziza-Laskar et al., *J. Appl. Polym. Sci.*, 50:651 (1993); Nurdin et al., *J. Appl. Polym. Sci.*, 50:663 (1993); Nurdin et al., *J. Appl. Polym. Sci.*, 50:671 (1993); Hazziza-Laskar et al., *J. Appl. Polym. Sci.*, 58:77 (1995)) which are then cast as films. Although these films are biocidal, their limitations are that they need long contact times to kill the organisms, the surface cannot be reactivated once the biocidal activity is lost, the films are relatively expensive to make, and the films are partially water soluble. Other types of surface active disinfectants are polymeric phosphonium materials (Kanazawa et al., *J. Polym. Sci.*, Part A: *Polym. Chem.*, 31:1467 (1993); *J. Appl. Polym. Sci.*, 52:641 (1994)), modified polyesters, polyethers and benzimidiazoles (Oh et al., *J. Appl. Polym. Sci.*, 52:583 (1994); *J. Appl. Polym. Sci.*, 54:859 (1994); Cho et al., *J. Macromol. Sci., Pure Appl. Chem.*, A32:479 (1995)) which are resistant to several types of microorganisms, but the biocidal moiety cannot be regenerated once exhausted, the films are costly to make, and they can be water soluble.

Therefore, there is a need for a surface active biocide that is inexpensive to manufacture, can regenerate its biocidal activity, is water insoluble when necessary, can kill a broad spectrum of microorganisms, does not affect its environment unfavorably, and requires relatively short contact times to inactivate microorganisms when necessary. There is also a need for the contact biocide to be applied to numerous substrates such as glass, wood, metal, fibrous materials, and concrete to maximize the applications for its use.

SUMMARY OF THE INVENTION

The present invention relates to a monomer and its corresponding polymers and copolymers comprising a cyclic N-halamine unit, wherein the cyclic N-halamine unit comprises: a 5-membered ring wherein 3 members of the ring are carbon, 1 member of the ring is a nitrogen heteroatom, and 1 member of the ring is oxygen heteroatom; wherein one carbon member comprises a carbonyl group; wherein one non-carbonyl carbon member is attached to an acryloxymethyl linkage which is substituted with moieties $R_2$, $R_3$, and $R_4$, which moieties are selected from the group consisting of hydrogen, $C_1$–$C_4$ alkyl, benzyl, substituted benzyl, phenyl and substituted phenyl; wherein said non-carbonyl carbon member is also joined to a moiety $R_1$ selected from the group consisting of hydroxyl, $C_1$–$C_4$ alkyl, benzyl, substituted benzyl, phenyl and substituted phenyl; and wherein the nitrogen heteroatom is joined to a moiety X selected from the group consisting of chlorine, bromine or hydrogen. The general structure for one embodiment of the monomer is shown below.

STRUCTURE I

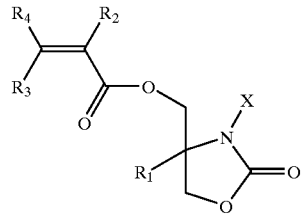

wherein X is chlorine, bromine or hydrogen; $R_1$ is selected from the group consisting of hydroxyl, $C_1$–$C_4$ alkyl, benzyl, substituted benzyl, phenyl and substituted phenyl; $R_2$, $R_3$ and $R_4$ are each independently selected from the group consisting of hydrogen, $C_1$–$C_4$ alkyl, benzyl, substituted benzyl, phenyl and substituted phenyl. A method of using the monomer of structure I for producing a biocidal material or coating through halogenation with chlorine or bromine is also disclosed. The biocidal material can be applied as a coating or film onto a plurality of substrates useful for their disinfectant properties. The biocidal properties can be regenerated by renewed halogenation in chlorine or bromine solutions.

The present invention also relates to biocidal polymers comprising a cyclic N-halamine unit linked at a carbon atom to a second N-halamine unit via acryloxymethyl linkage wherein each N-halamine unit comprises a 5 membered ring, wherein 3 members of the ring are carbon, 1 member of the ring is nitrogen heteroatom, and 1 member of the ring is oxygen heteroatom; wherein 1 carbon member comprises a carbonyl group; wherein 1 non-carbonyl carbon member is linked to the second N-halamine unit via acryloxymethyl linkage, which linkage is substituted with moieties $R_2$, $R_3$ and $R_4$ each of which are independently selected from the group consisting of hydrogen, $C_1$–$C_4$ alkyl, phenyl, substituted phenyl, benzyl, substituted benzyl; wherein said non-carbonyl carbon member is also joined to an $R_1$ substituent selected from the group consisting of hydroxyl, $C_1$–$C_4$ alkyl, phenyl, substituted phenyl, benzyl, substituted benzyl; and wherein the nitrogen heteroatom is joined to a moiety X selected from the group consisting of chlorine and bromine.

The invention also relates to biocidal copolymers comprising a cyclic N-halamine monomeric unit linked at a carbon atom by an acryloxymethyl linkage to a second monomeric unit, wherein the second monomeric unit is any polymerizable olefin, e.g., acrylic acid, vinyl acetate, vinyl chloride, styrene, acrylonitrile, propylene, or ethylene; wherein the N-halamine monomeric unit comprises a 5 membered ring, wherein 3 members of the ring are carbon, 1 member of the ring is nitrogen heteroatom, and 1 member of the ring is oxygen heteroatom; wherein 1 carbon member comprises a carbonyl group; wherein I non-carbonyl carbon member is linked to the second monomeric unit via acryloxymethyl linkage, which linkage is substituted with moieties $R_2$, $R_3$ and $R_4$ each of which are independently selected from the group consisting of hydrogen, $C_1$–$C_4$ alkyl, phenyl, substituted phenyl, benzyl and substituted benzyl; wherein said non-carbonyl carbon member is also joined to an $R_1$ substituent selected from the group consisting of hydroxyl, $C_1$–$C_4$ alkyl, phenyl, substituted phenyl, benzyl and substituted benzyl; and wherein the nitrogen heteroatom is joined to a moiety X selected from the group consisting of chlorine and bromine.

The invention also relates to biocidal grafted copolymers comprising a cyclic N-halamine unit linked at a carbon atom by an acryloxymethyl linkage to a polymer backbone wherein the polymer backbone is any commercial polymer, e.g., poly-vinyl chloride, poly-acrylonitrile, poly-vinyl acetate, poly-vinyl alcohol, poly-styrene, cellulose, and cellulose blends with polyester, rayon, spandex, and polyurethanes; wherein the N-halamine unit comprises a 5 membered ring, wherein 3 members of the ring are carbon, 1 member of the ring is nitrogen heteroatom, and 1 member of the ring is oxygen heteroatom; wherein 1 carbon member comprises a carbonyl group; wherein 1 non-carbonyl carbon member is linked to the polymer via acryloxymethyl linkage, which linkage is substituted with moieties $R_2$, $R_3$ and $R_4$ each of which are independently selected from the group consisting of hydrogen, $C_1$–$C_4$ alkyl, phenyl, substituted phenyl, benzyl and substituted benzyl; wherein said non-carbonyl carbon member is also joined to a substituent $R_1$ selected from the group consisting of hydroxyl, $C_1$–$C_4$ alkyl, phenyl, substituted phenyl, benzyl and substituted benzyl; and wherein the nitrogen heteroatom is joined to a moiety X selected from the group consisting of chlorine and bromine.

The present invention further relates to another monomer and its corresponding polymers and copolymers, the monomer comprising a cyclic N-halamine unit, wherein the cyclic N-halamine unit comprises: a 5-membered ring wherein 3 members of the ring are carbon, 2 members of the ring are nitrogen heteroatoms; wherein two carbon members each comprise a carbonyl group; wherein one nitrogen heteroatom is attached to an acryloxymethyl linkage which is substituted with moieties $R_3$, $R_4$, and $R_5$, which moieties are selected from the group consisting of hydrogen, $C_1$–$C_4$ alkyl, benzyl, substituted benzyl, phenyl and substituted phenyl; wherein the remaining non-carbonyl carbon member is also joined to moieties $R_1$ and $R_2$ selected from the group consisting of hydrogen, hydroxyl, $C_1$–$C_4$ alkyl, benzyl, substituted benzyl, phenyl and substituted phenyl; and wherein the remaining nitrogen heteroatom is joined to a moiety X selected from the group consisting of chlorine, bromine or hydrogen. The general structure for one embodiment of the monomer is shown as structure IV below.

STRUCTURE IV

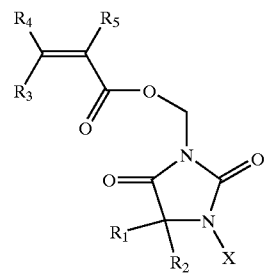

A method of using the monomer of structure IV for producing a biocidal material or coating through halogenation with chlorine or bromine is also disclosed. The biocidal material can be applied as a coating or film onto a plurality of substrates useful for their disinfectant properties. The biocidal properties can be regenerated by renewed halogenation in chlorine or bromine solutions.

The present invention further relates to a chemical unit useful to produce monomers and corresponding polymers and copolymers which are used to produce biocides, the unit comprising a cyclic N-halamine unit, wherein the cyclic N-halamine unit comprises: a 5-membered ring wherein 3 members of the ring are carbon, and 2 members of the ring are nitrogen heteroatoms; wherein two carbon members each comprise a carbonyl group; one nitrogen heteroatom is attached to a hydroxymethyl group and the remaining is attached to a hydrogen and the remaining non-carbonyl carbon member is joined to moieties $R_1$ and $R_2$ selected from the group consisting of hydrogen, hydroxyl, $C_1$–$C_4$ alkyl, benzyl, substituted benzyl, phenyl and substituted phenyl. The general structure for one embodiment of the unit is shown as structure III below.

STRUCTURE III

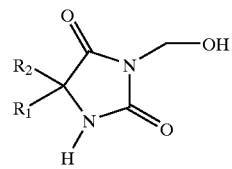

A method of using the unit of structure III for producing monomers by condensation of the unit with a diisocyanate or polyurethane in the presence of a tertiary amine, wherein the monomers are useful in producing biocidal materials and coatings by polymerization, and followed by halogenation with chlorine or bromine, is also disclosed. The biocidal material can be applied as a coating or film onto a plurality of substrates useful for their disinfectant properties. The biocidal properties can be regenerated by renewed halogenation with chlorine or bromine solutions.

The present invention further relates to another monomer and its corresponding polymers and copolymers, the monomer comprising a cyclic N-halamine unit, wherein the cyclic N-halamine unit comprises: a 5-membered ring wherein 3 members of the ring are carbon, and 1 member of the ring is nitrogen heteroatom, and the remaining member of the ring is oxygen heteroatom; wherein one carbon member comprises a carbonyl group; the nitrogen heteroatom is attached to a hydrogen and one of the remaining carbons is attached to 2 hydroxymethyl groups. The general structure for one embodiment of the monomer is shown as structure V below.

STRUCTURE V

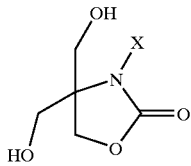

A method of using the monomer of structure V for producing a biocidal material or coating by polymerization with a diisocyanate or polyurethane in the presence of a tertiary amine, followed by halogenation with chlorine or bromine is also disclosed. In one actual embodiment, a diol can be included in the polymerization step. The biocidal material can be applied as a coating or film onto a plurality of substrates useful for their disinfectant properties. The biocidal properties can be regenerated by renewed halogenation in chlorine or bromine solutions.

The invention further relates to a method for disinfecting a habitat for halogen-sensitive microorganisms comprising contacting the habitat with a N-halamine monomer, polymer, copolymer or grafted copolymer as described above.

The present invention provides an improved compound and method of using the same for disinfecting a habitat for halogen-sensitive microorganisms, and further provides novel N-halamine biocidal compounds in surface coatings for disinfection of halogen-sensitive organisms.

DETAILED DESCRIPTION OF THE PREFERRED EMBODIMENT

The present invention may be understood more readily by reference to the following detailed description of specific embodiments and the Examples and Figures included therein.

As used herein, "precursor" or "intermediate" compound can mean a single chemical unit, or its derivatives, a monomer, or its derivatives, or any chain of units, derivatives, and monomers which have been polymerized, co-polymerized, or grafted with each other or with units, derivatives, or monomers.

As used herein, "cyclic N-halamine unit" refers to a heterocyclic, monocyclic compound wherein the ring members comprise at least carbon, nitrogen, and oxygen provided there is at least one nitrogen heteroatom; wherein at least one halogen, preferably chlorine or bromine, is bonded to a nitrogen heteroatom; and wherein at least one carbon ring member can comprise a carbonyl group. The presence of the halogen renders it biocidal. The term "cyclic amine unit" refers to a heterocyclic, monocyclic compound wherein the ring members comprise at least carbon, nitrogen, and oxygen provided there is at least one nitrogen heteroatom; wherein hydrogen is bonded to a nitrogen heteroatom; and wherein at least one carbon ring member can comprise a carbonyl group. Methods described herein for preparing polymers using cyclic N-halamine monomers can readily be performed with cyclic amine monomers.

Herein, "polymer" and "copolymer" are at times used interchangeably. The use of one or the other term is not meant to be limiting except where indicated by the context.

As used herein, the term "a polymer comprising a cyclic amine or N-halamine unit joined by a linkage to a second cyclic amine or N-halamine unit" is not meant to be limiting as to the number of cyclic amine or N-halamine units in a polymer. A "polymer" can comprise two or more cyclic amine or N-halamine units, and the number of units in any given polymer can vary according to the use intended for the polymer. For example, the polymer can comprise 2, 3, 4, 5, 6, 7, 8, 9, 10, 20, 25, 30, 40, 50, 75, 100, 150, 200, 250, 500, 1000, and so forth, units.

Additionally, a "polymer comprising a cyclic amine unit joined by a linkage to a second cyclic amine unit" or a "biocidal polymer comprising a cyclic N-halamine unit joined by a linkage to a second cyclic N-halamine unit" can further comprise additional, other monomer types, which can be designated monomer "M" or monomer "O," for example, for convenience (i.e., a copolymer). Each cyclic amine or N-halamine unit in the polymer can be identical or they can vary. A polymer/copolymer can comprise, for example, one, two, three, four, five, ten or more different monomers. The monomers can be arranged in random arrangement or in block arrangement. A "biocidal polymer" of this invention can comprise one or more biocidal cyclic N-halamine units, i.e., halogenated cyclic amine units.

As used herein, a "biocidal N-halamine copolymer comprising N-halamine unit joined by an acryloxymethyl linkage to a second monomeric unit" is not meant to be limiting as to the number of cyclic N-halamine units in a polymer, nor is it meant to suggest that each cyclic N-halamine unit is linked to a different monomeric unit. It refers to a copolymerization of the cyclic amine with one or more different monomeric units in a controlled or random array in the polymer. A "copolymer" can comprise two or more cyclic N-halamine units, and one or more different monomeric units and the number of units in any given copolymer can vary according to the use of the copolymer.

The copolymer can be prepared in bulk, solution, emulsion, or suspension depending on the application desired. A "bulk" copolymerization can comprise cyclic amine monomer and at least one other monomer wherein the polymerization occurs in the absence of solvent. A "solution" copolymerization can comprise cyclic amine monomer and at least one other monomer wherein the polymerization occurs in a solvent, either organic or inorganic. An "emulsion" copolymerization can comprise cyclic amine monomer and at least one other monomer wherein the polymerization occurs where water is the solvent along with a surfactant. A "suspension" copolymerization can comprise cyclic amine monomer and at least one other monomer wherein the polymerization occurs where water is the solvent. Each cyclic N-halamine unit and monomeric unit in the copolymer can be identical. A "latex" is any polymer that is emulsified in water via surfactant or any other emulsifying agent. An example of the nomenclature used throughout for all copolymerizations goes as follows: poly-acrylonitrile-co-3-chloro-4-(acryloxymethyl)-4-ethyl-2-oxazolidinone.

As used herein, a "biocidal N-halamine grafted copolymer comprising a N-halamine unit joined by an acryloxymethyl linkage to a polymer backbone" is not meant to be limiting as to the number of cyclic N-halamine units in a polymer, nor is it meant to suggest that each cyclic N-halamine unit is directly linked to the polymer backbone. It refers to chemically grafting two or more cyclic amine units on to a pre-existing polymeric backbone in a specific or random arrangement. A "grafted copolymer" can comprise a polymer backbone wherein the polymer is comprised of one or more monomeric units which can be polymeric cyclic N-halamines. A grafting reaction can occur in solution or bulk. Each cyclic N-halamine unit and polymeric backbone in the grafted copolymer can be identical, they can be repeat motifs of two or more units, or they can be a random arrangement of two or more different units. An example of the nomenclature used throughout for all grafting reactions is as follows: poly-acrylonitrile-g-3-chloro-4-(acryloxymethyl)-4-ethyl-2-oxazolidinone.

As used herein, a "habitat for halogen-sensitive microorganisms" is any substance in which or on which such organisms are capable of survival for a predetermined and undesirable period of time.

Cyclic organic N-halamine compounds having two alkyl substituent groups substituted on the ring carbons adjacent to the N—Cl and N—Br moieties exhibit long-term stability in aqueous solution and release little or no free halogen, while providing adequate disinfection efficacy. Additionally, because polymeric molecules can be constructed to have low solubility in water, an insoluble cyclic N-halamine polymer containing similar cyclic N-halamine structural groups is an ideal polymeric biocide.

A strategy for incorporating cyclic N-halamine structural groups into polymers is: an existing cyclic amine or amide such as those described by Worley in U.S. Pat. Nos. 4,681,948; 4,767,542; 5,057,612; 5,126,057 is functionalized with a polymerizable moiety such as a vinyl group and then polymerized and halogenated. The insoluble cyclic N-halamine polymers inactivate microorganisms once applied to a substrate upon contact, release minimal amounts of free halogen and other leachable impurities, and can be prepared or regenerated by applying diluted solutions of free halogen to the coated substrate containing the cyclic amine or amide.

A second strategy for incorporating cyclic N-halamine structural groups into polymers is to modify an existing polymer by linking a biocidal moiety to it as in Worley U.S. Pat. No. 5,490,983. The former strategy is more preferable in the current embodiment.

The novel N-halamine biocidal polymers described herein contain heterocyclic units which have stable N—Cl or N—Br chemical bonds necessary for biocidal action. The heterocyclic N-halamine units can comprise 5 membered rings, wherein at least one heteroatom is nitrogen and at least one heteroatom is oxygen, and which can have one carbonyl group. A carbon atom of these heterocyclic moieties can be joined by a linkage to an additional heterocyclic N-halamine unit by one of many possible linkages which attach to each N-halamine unit at a single non-carbonyl carbon atom, such as by a lower alkyl, i.e., a three to eleven carbon chain that can be branched when greater than three carbons, or a phenyl-lower alkyl-phenyl i.e., two phenyl groups joined by a three to eleven carbon chain that can be branched when greater than three carbons wherein one phenyl attaches to a cyclic N-halamine unit and the other phenyl attaches to a neighboring cyclic N-halamine unit.

Specifically, compounds can include biocidal monomers comprising a cyclic N-halamine unit wherein the cyclic N-halamine unit comprises: a 5-membered ring, wherein at least 3 members of the ring are carbon, 1 member of the ring is nitrogen heteroatom, and 1 member is oxygen heteroatom; wherein 1 carbon member comprises a carbonyl group; wherein one non-carbonyl carbon member is attached to an acryloxymethyl linkage which is substituted with moieties $R_2$, $R_3$, and $R_4$, which moieties are selected from the group consisting of hydrogen, $C_1$–$C_4$ alkyl, benzyl, substituted benzyl, phenyl and substituted phenyl; wherein said non-carbonyl carbon member is also joined to a moiety $R_1$ selected from the group consisting of hydroxyl, $C_1$–$C_4$ alkyl, benzyl, substituted benzyl, phenyl and substituted phenyl; and wherein the nitrogen heteroatom is joined to a moiety X selected from the group consisting of chlorine and bromine.

Thus the present invention provides a monomer and its corresponding polymers and copolymers comprising a cyclic N-halamine unit, wherein the cyclic N-halamine unit comprises: a 5-membered ring wherein 3 members of the ring are carbon, 1 member of the ring is a nitrogen heteroatom, and 1 member of the ring is oxygen heteroatom; wherein 1 carbon member comprises a carbonyl group; wherein one non-carbonyl carbon member is attached to an acryloxymethyl linkage which is substituted with moieties $R_2$, $R_3$, and $R_4$, which moieties are selected from the group consisting of hydrogen, $C_1$–$C_4$ alkyl, benzyl, substituted benzyl, phenyl and substituted phenyl; wherein said non-carbonyl linkage carbon member is also joined to a moiety $R_1$ selected from the group consisting of hydroxyl, $C_1$–$C_4$ alkyl, benzyl, substituted benzyl, phenyl and substituted phenyl; and wherein the nitrogen heteroatom is joined to a moiety X selected from the group consisting of chlorine, bromine or hydrogen. A general structure for one embodiment of the monomer is shown below.

STRUCTURE I

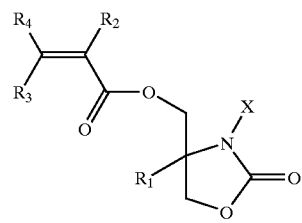

wherein X is chlorine, bromine or hydrogen; $R_1$ is selected from the group consisting of hydroxyl, $C_1$–$C_4$ alkyl, benzyl, substituted benzyl, phenyl and substituted phenyl; $R_2$, $R_3$ and $R_4$ are each independently selected from the group consisting of hydrogen, $C_1$–$C_4$ alkyl, benzyl, substituted benzyl, phenyl and substituted phenyl. The monomer is biocidal when X is chlorine or bromine.

Compounds also include biocidal polymers comprising a cyclic N-halamine unit linked at a carbon atom by acryloxymethyl linkage to a second cyclic N-halamine unit, wherein each cyclic N-halamine unit is a 5-membered ring, wherein 3 members of the ring are carbon, and 1 member of the ring is nitrogen heteroatom; wherein 1 member of the ring is oxygen heteroatom; wherein 1 carbon member comprises a carbonyl group; wherein 1 non-carbonyl carbon member is attached to an acryloxymethyl linkage which is substituted with moieties $R_2$, $R_3$, and $R_4$, which moieties are selected from the group consisting of hydrogen, $C_1$–$C_4$ alkyl, benzyl, substituted benzyl, phenyl and substituted phenyl; wherein said non-carbonyl linkage carbon member is also joined to a moiety $R_1$ selected from the group consisting of hydroxyl, $C_1$–$C_4$ alkyl, benzyl, substituted benzyl, phenyl and substituted phenyl; and wherein the nitrogen heteroatom is joined to a moiety X selected from the group consisting of chlorine, bromine or hydrogen.

Compounds also include biocidal copolymers comprising one or more cyclic N-halamine units linked at a carbon atom by acryloxymethyl linkage to a second monomeric unit, wherein the second monomeric unit can be any polymerizable olefin.

Compounds also include biocidal grafted copolymers comprising one or more cyclic N-halamine units linked at a carbon atom by acryloxymethyl linkage to a pre-existing polymer backbone, wherein the polymeric backbone can be any commercial polymer.

Examples of the aforementioned polymers, copolymers and grafted copolymers include, but are not limited to, polymers, copolymers and grafted copolymers comprising one or more cyclic amine and N-halamine monomers represented by the repeating unit graphic formula illustrated below.

STRUCTURE II

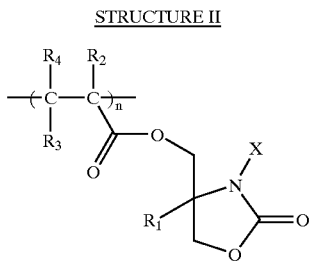

wherein X is selected from the group consisting of hydrogen, chlorine, and bromine but when X is hydrogen, no biocidal activity is imparted; wherein $R_1$ is selected from the group consisting of hydroxyl, $C_1$–$C_4$ alkyl, benzyl, substituted benzyl, phenyl, substituted phenyl, and any combination thereof; and wherein $R_2$, $R_3$, and $R_4$ are each independently selected from the group consisting of hydrogen, $C_1$–$C_4$ alkyl, benzyl, substituted benzyl, phenyl, and substituted phenyl.

The alkyl substituents representing $R_1$, $R_2$, $R_3$, and $R_4$ or those attached to phenyl or benzyl may contain from 1 to 4 carbon atoms, including methyl, ethyl, propyl, isopropyl, n-butyl, isobutyl, secondary butyl, and tertiary butyl. As shown by the graphic formulae, the linkages between two cyclic N-halamine units can be a "lower alkyl" defined as a hydrocarbon chain, branched or unbranched, having three carbon atoms. For example, a structure II polymer may contain a three carbon linkage, wherein $R_1$ is methyl, and $R_2$, $R_3$, and $R_4$ are hydrogen.

Examples of the aforementioned compounds for each structure type include, but are not limited to: structure I: 3-chloro-4-(acryloxymethyl)-4-ethyl-2-oxazolidinone; 3-bromo-4-(acryloxymethyl)-4-ethyl-2-oxazolidinone; structure II: poly-3-chloro-4-(acryloxymethyl)-4-ethyl-2-oxazolidinone; poly-3-bromo-4-(crotonoxymethyl)-4-ethyl-2-oxazolidinone; poly-acrylonitrile-co-3-chloro-4-(acryloxymethyl)-4-ethyl-2-oxazolidinone; poly-acrylonitrile-co-3-bromo-4-(acryloxymethyl)-4-ethyl-2-oxazolidinone; poly-acrylic acid-co-3-chloro-4-(acryloxymethyl)-4-ethyl-2-oxazolidinone; poly-styrene-co-3-chloro-4-(acryloxymethyl)-4-ethyl-2-oxazolidinone; poly-vinyl acetate-co-3-chloro-4-(acryloxymethyl)-4-ethyl-2-oxazolidinone; poly-vinyl chloride-co-3-chloro-4-(acryloxy-methyl)-4-ethyl-2-oxazolidinone; poly-acrylonitrile-g-3-chloro-4-(acryloxymethyl)-4-ethyl-2-oxazolidinone; poly-vinyl chloride-g-3-chloro-4-(acryloxymethyl)-4-ethyl-2-oxazolidinone; poly-styrene-g-3-chloro-4-(acryloxymethyl)-4-ethyl-2-oxazolidinone; poly-vinyl acetate-g-3-chloro-4-(acryloxymethyl)-4-ethyl-2-oxazolidinone; poly-vinyl alcohol-g-3-chloro-4-(acryloxymethyl)-4-ethyl-2-oxazolidinone.

By substitution of other named substituents for $R_1$, $R_2$, $R_3$, and $R_4$, e.g., propyl, phenyl, etc., for one or more of the derivatives above named, other correspondingly named N-halo derivatives may be formed.

The polymeric N-halamine biocidal compounds of the present invention can be prepared by reacting the corresponding unhalogenated polymers, herein referred to as "precursor cyclic amines" or "cyclic amines," with a source of chlorine or bromine. While chlorine gas or liquid bromine may be utilized, other milder halogenating agents such as, but not limited to, calcium hypochlorite, sodium hypochlorite, N-chlorosuccinimide, N-bromosuccinimide, sodium dichloroisocyanurate, trichloroisocyanuric acid, tertiary butyl hypochlorite, N-chloroacetamide, N-chloramines, N-bromamines, etc., can also be employed. Halogenation of the unhalogenated compounds can be accomplished in aqueous media, in mixtures of water with common inert organic solvents such as methylene chloride, chloroform, and carbon tetrachloride, in inert organic solvents themselves, or with no solvent present, at room temperature. The precursor cyclic amines can be a previously utilized cyclic N-halamine that has become ineffective at killing microorganisms due to inactivation of the N—Cl or N—Br moieties. The above-described halogenations can be performed in situ, if desired.

The unhalogenated precursor cyclic amines described in this invention can be prepared from existing inexpensive commercial grade starting materials. In the case of the structure represented above by structure I, commercial grade 2-amino-2-alkyl-1,3-propanediols can be reacted with dialkyl carbonates in the presence of sodium methoxide or sodium ethoxide as a catalyst in common solvents in a cyclization reaction to produce the 4-alkyl-4-hydroxymethyl-2-oxazolidinone, followed by reaction with acryloyl chloride, or substituted acryloyl chlorides in common solvents such as chloroform, methylene chloride, benzene, toluene, acetone, etc., to produce the 4-(acryloxymethyl)-4-alkyl-2-oxazolidinone. Those who are skilled in the art know that the 4-alkyl-4-hydroxymethyl-2-oxazolidinone could be prepared by other synthetic strategies. For the structures represented by structure II, the compounds encompassing those in structure I are homopolymerized in the presence of an organic soluble initiator, such as, but not limited to, 1,1'-azobis(cyclohexanecarbonitrile), 2,2'-azobisisobutyronitrile, substituted 2,2'-azobisisobutyronitrile, benzoyl peroxide, substituted benzoyl peroxide, etc., or a water soluble initiator, such as, but not limited to, hydrogen peroxide, ammonium persulfate, sodium persulfate, potassium persulfate, etc., in the presence of a surfactant, such as, but not limited to, sodium laurel sulfate, ammonium laurel sulfate, etc., when water is used as the solvent, and in common solvents such as, chloroform, methylene chloride, carbon tetrachloride, dimethylformamide, etc. For copolymerizations, the compounds encompassing those in structure I-type are copolymerized with various monomers, such as, but not limited to, acrylonitrile, acrylic acid, ethylene, propylene, styrene, vinyl acetate, vinyl chloride, etc., in the presence of an initiator as mentioned above, in solvents as mentioned above, and with a surfactant as mentioned above. For grafting reactions, the compounds encompassing structure I-type are grafted on to polymeric backbones, such as, but not limited to, poly-acrylonitrile, poly-acrylic acid, poly-styrene, poly-vinyl acetate, poly-vinyl alcohol, poly-vinyl chloride, etc., in the presence of an initiator as mentioned above, with the addition of a surfactant as mentioned above. The polymeric backbone is in latex form, which means it is emulsified in water prior to the grafting reaction either with surfactants for water soluble polymers, i.e., poly-vinyl alcohol, poly-acrylic acid, etc., or for water insoluble polymers, i.e., poly-acrylonitrile, poly-vinyl chloride, poly-styrene, etc.; the corresponding monomers, i.e., acrylonitrile, vinyl chloride, styrene, etc., are polymerized in an emulsion prior to the grafting reaction.

The present invention further provides a method for disinfecting a habitat for halogen-sensitive microorganisms comprising contacting the habitat with a biocidal amount of a biocidal monomer as described herein. For example, the biocidal monomer can be any of the following, used singly or in combination:

3-chloro-4-(acryloxymethyl)-4-ethyl-2-oxazolidinone,
3-chloro-4-(crotonoxymethyl)-4-ethyl-2-oxazolidinone,
3-chloro-4-(2'-methylacryloxymethyl)-4-ethyl-2-oxazolidinone,
3-chloro-4-(3',3'-dimethylacryloxymethyl)-4-ethyl-2-oxazolidinone,
3-bromo-4-(acryloxymethyl)-4-ethyl-2-oxazolidinone,
3-bromo-4-(crotonoxymethyl)-4-ethyl-2-oxazolidinone,
3-bromo-4-(2'-methylacryloxymethyl)-4-ethyl-2-oxazolidinone, and
3-bromo-4-(3',3'-dimethylacryloxymethyl)-4-ethyl-2-oxazolidinone.

The present invention further provides a method for disinfecting a habitat for halogen-sensitive microorganisms comprising contacting the habitat with a biocidal amount of a biocidal polymer as described herein. For example, the biocidal polymer can be any of the following, used singly or in combination:

poly-3-chloro-4-(acryloxymethyl)-4-ethyl-2-oxazolidinone,
poly-3-chloro-4-(crotonoxymethyl)-4-ethyl-2-oxazolidinone,
poly-3-chloro-4-(2'-methylacryloxymethyl)-4-ethyl-2-oxazolidinone,
poly-3-chloro-4-(3',3'-dimethylacryloxymethyl)-4-ethyl-2-oxazolidinone,
poly-acrylonitrile-co-3-chloro-4-(acryloxymethyl)-4-ethyl-2-oxazolidinone,
poly-styrene-co-3-chloro-4-(acryloxymethyl)-4-ethyl-2-oxazolidinone,
poly-vinyl acetate-co-3-chloro-4-(acryloxymethyl)-4-ethyl-2-oxazolidinone,
poly-vinyl chloride-co-3-chloro-4-(acryloxymethyl)-4-ethyl-2-oxazolidinone,
poly-ethylene-co-3-chloro-4-(acryloxymethyl)-4-ethyl-2-oxazolidinone,
poly-propylene-co-3-chloro-4-(acryloxymethyl)-4-ethyl-2-oxazolidinone,
poly-acrylonitrile-g-3-chloro-4-(acryloxymethyl)-4-ethyl-2-oxazolidinone,
poly-styrene-g-3-chloro-4-(acryloxymethyl)-4-ethyl-2-oxazolidinone,
poly-vinyl acetate-g-3-chloro-4-(acryloxymethyl)-4-ethyl-2-oxazolidinone,
poly-vinyl alcohol-g-3-chloro-4-(acryloxymethyl)-4-ethyl-2-oxazolidinone,
poly-vinyl chloride-g-3-chloro-4-(acryloxymethyl)-4-ethyl-2-oxazolidinone,
poly-ethylene-g-3-chloro-4-(acryloxymethyl)-4-ethyl-2-oxazolidinone,
poly-propylene-g-3-chloro-4-(acryloxymethyl)-4-ethyl-2-oxazolidinone,
cellulose-g-3-chloro-4-(acryloxymethyl)-4-ethyl-2-oxazolidinone,
poly-3-bromo-4-(acryloxymethyl)-4-ethyl-2-oxazolidinone,
poly-3-bromo-4-(crotonoxymethyl)-4-ethyl-2-oxazolidinone,
poly-3-bromo-4-(2'-methylacryloxymethyl)-4-ethyl-2-oxazolidinone,
poly-3-bromo-4-(3',3'-dimethylacryloxymethyl)-4-ethyl-2-oxazolidinone,
poly-acrylonitrile-co-3-bromo-4-(acryloxymethyl)-4-ethyl-2-oxazolidinone,
poly-styrene-co-3-bromo-4-(acryloxymethyl)-4-ethyl-2-oxazolidinone,
poly-vinyl acetate-co-3-bromo-4-(acryloxymethyl)-4-ethyl-2-oxazolidinone,
poly-vinyl chloride-co-3-bromo-4-(acryloxymethyl)-4-ethyl-2-oxazolidinone,
poly-ethylene-co-3-bromo-4-(acryloxymethyl)-4-ethyl-2-oxazolidinone,
poly-propylene-co-3-bromo-4-(acryloxymethyl)-4-ethyl-2-oxazolidinone,
poly-acrylonitrile-g-3-bromo-4-(acryloxymethyl)-4-ethyl-2-oxazolidinone,
poly-styrene-g-3-bromo-4-(acryloxymethyl)-4-ethyl-2-oxazolidinone,
poly-vinyl acetate-g-3-bromo-4-(acryloxymethyl)-4-ethyl-2-oxazolidinone,
poly-vinyl alcohol-g-3-bromo-4-(acryloxymethyl)-4-ethyl-2-oxazolidinone,
poly-vinyl chloride-g-3-bromo-4-(acryloxymethyl)4-ethyl-2-oxazolidinone,
poly-ethylene-g-3-bromo-4-(acryloxymethyl)-4-ethyl-2-oxazolidinone,
poly-propylene-g-3-bromo-4-(acryloxymethyl)-4-ethyl-2-oxazolidinone, and
cellulose-g-3-bromo-4-(acryloxymethyl)-4-ethyl-2-oxazolidinone.

The cyclic N-halamine biocidal compounds can be made soluble or insoluble in water depending on the application desired. They can be employed as disinfectants against undesirable microorganisms in many habitats including surfaces of materials by treating the material with a biocidally effective amount of polymer compound. Water insoluble biocidal surfaces can include the following applications: for example, oil and water based paints, catheters, surgical tables, surgical instrumentation, medical tables and desktops, medical instrumentation, dental tables and desktops, dental instrumentation, swimming pool liners, fabric materials, medical wrappings, piping, workbenches, counter tops, and the like. Water soluble biocidal surfaces can include the following applications, for example, oil and gas tank liners, preservatives, can and bag liners, water based paints, and the like. As used herein, a "surface" can include any surface upon which halogen-sensitive microorganisms can dwell and to which a claimed polymer can be bound, which can include surfaces of, for example, textile fabric, metal, rubber, concrete, wood, glass, bandaging, and plastic.

For surfaces, disinfection testing is best accomplished by placing microbiologically contaminated water onto the polymer coated substrate. The contact time will be measured, which is the amount of time needed for the surface to kill a substantial amount of the microorganism; depending on the application, the contact times will vary. These polymeric biocides can be incorporated into textile and solid surfaces which can serve as disinfectants or biological preservatives.

Once a surface becomes ineffective at killing microorganisms due to inactivation of the N—Cl or N—Br moieties, it can be regenerated by wiping an aqueous solution of free halogen over it. Additionally, the cyclic N-halamine biocide can be created or regenerated in situ by adding a stoichiometric amount of free halogen, either chlorine or bromine, to a precursor cyclic amine contained in a material such as in paint, oil, textile fabric or the like, or bound to a surface of a material such as wood, glass, plastic polymer coating, textile fabric, metal, rubber, concrete, cloth bandage, or the like.

All microorganisms on hard surfaces susceptible to disinfection by free halogen, e.g., free chlorine, or combined halogen, e.g., N-haloimidazolidinones, N-halohydantoins, N-halooxazolidinones, N-haloisocyanurates, etc., will also be susceptible to disinfection by the biocidal compounds of this invention. Such microorganisms include, for example, bacteria, protozoa, fungi, viruses, and algae.

The biocidal compounds described herein can be employed in a variety of disinfecting applications. They will be of importance in controlling microbiological contamination on surfaces, for medical and dental applications, bandages, fabric materials, piping, paints, swimming pools, catheters, and the like. For example, the halogenated polymers will prevent the growth of undesirable organisms, such as the bacteria genera Staphylococcus, Pseudomonas, Salmonella, Shigella, Legionella, Methylobacterium, Klebsiella, and Bacillus; the fungi genera Candida, Rhodoturula, and molds such as mildew; the protozoa genera Giardia, Entamoeba, and Cryptosporidium; the viruses poliovirus, rotavirus, HIV, and herpesvirus; and the algae genera Anabaena, Oscillatoria, and Chlorella; and other sources of biofouling on surfaces. They will be of importance as preservatives and preventatives against microbiological contamination in paints, coatings, and on surfaces. They will be of particular importance to the medical field for use in ointments, bandages, sterile surfaces, and the like, and for the attachment to liners of containers used in the food processing industry. They can be used in conjunction with textiles for sterile applications, such as coatings or physical bonds to sheets or bandages used for burn victims or on microbiological decontamination suits.

The halogenated compounds described herein can be used in diverse liquid and solid formulations such as powders, granular materials, solutions, concentrates, emulsions, slurries, and in the presence of diluents, extenders, fillers, conditioners, aqueous solvent, organic solvents, plasticizers, pigments, and the like. Of particular use can be their employment in formulations involving wetting emulsifying, or dispersing agents such as sulfonates, alcohols, or similar surface active materials. The compounds are also compatible with buffering agents and other sources of halogen.

A further embodiment of biocidal compounds made in accordance with the invention uses monomers of:

3-hydroxymethyl-5,5-dimethylhydantoin (Structure III, wherein $R_1$ and $R_2$ are methyl),

STRUCTURE III

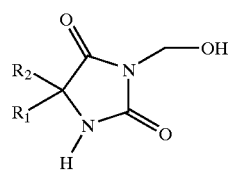

3-(acryloxymethyl)-5,5-dimethylhydantoin (Structure IV, wherein $R_1$ and $R_2$ are methyl, and $R_3$, $R_4$, and $R_5$ are hydrogen) and,

STRUCTURE IV

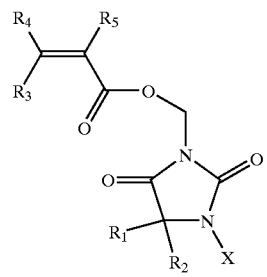

4,4-dihydroxymethyl-2-oxazolidinone (Structure V)

STRUCTURE V

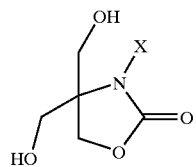

in synthesizing polymers, copolymers, and grafted copolymers which can be coated onto surfaces and upon halogenation with free chlorine or bromine, become biocidal. Of particular importance is the use of these monomers in the preparation of the N-chlorinated copolymers of 3-(acryloxymethyl)-5,5-dimethylhydantoin and methyl methacrylate/2-hydroxyethyl acrylate or methyl methacrylate/acrylic acid for biocidal thermosetting coatings, and in the preparation of N-chlorinated copolymers of 4,4-dihydroxymethyl-2-oxazolidinone and diisocyanates. The latter class of compounds is preferably used for biocidal polyurethane coatings.

The present invention is more particularly described in the following examples which are intended as illustrative only since numerous modifications and variations therein will be apparent to those skilled in the art.

EXAMPLES

Example 1

Preparation of 3-halo-4-(acryloxymethyl)4-ethyl-2-oxazolidinone (1a-Cl, 1a-Br)

To a one-neck round bottom flask were added 13.7 grams (0.115 mole) 2-amino-2-ethyl-1,3-propanediol (Aldrich Chemical Co., Milwaukee, Wis.), 17.5 milliliters (0.144 mole) diethylcarbonate, and 0.10 grams (0.0019 mole) sodium methoxide. The reagents were heated to 110° C. and refluxed with stirring for forty-eight hours. The reflux condenser was then removed and replaced with a distillation head. The ethanol was then removed by simple distillation, and the thick residue was cooled to room temperature. 100 milliliters ethyl acetate was then added to the residue, and the solution was vigorously stirred. Slowly a white solid formed. The solid was vacuum filtered to give 13.34 grams (80% of yield theoretically expected) 4-hydroxymethyl-4-ethyl-2-oxazolidinone as a white powder. The product exhibited a melting point of 75–77° C.; and the following spectral characteristics: $^1$H NMR (CDCl$_3$) δ0.91(t, 3H J=7.5 Hz), 1.53–1.65(m, 2H), 3.31(s, 2H), 3.92(d, 1H J=2.4 Hz), 4.13(d, 1H J=2.4 Hz), 5.83(s, 1H), 7.46 (s, 1H); $^{13}$C NMR (CDCl$_3$) δ7.7, 28.2, 62.6, 66.2, 71.2, 160.8; IR (KBr) 3316, 3245, 2967, 1727 cm$^{-1}$; MS m/z 145.

3.10 grams (0.021 mole) of the 4-hydroxymethyl-4-ethyl-2-oxazolidinone prepared as described above, 2.0 grams (0.022 mole) acryloyl chloride, and 25 milliliters chloroform were mixed in a one-neck round-bottom flask. The heterogeneous solution was heated to reflux, with stirring, for six hours, at which time all of the solid had dissolved. The solution was cooled to room temperature, and the solvent was removed under reduced pressure. 4.10 grams (98% of the yield theoretically expected) 4-(acryloxymethyl)-4-ethyl-2-oxazolidinone (1a) was obtained as a yellow oil. The product exhibited the following spectral data: $^1$H NMR (CDCl$_3$) δ0.88(t, 3H J=1.8 Hz), 1.53–1.66(m, 2H), 3.99–4.18(m, 4H), 5.83(d, 1H J=2.4 Hz), 5.98–6.10(m, 1H), 6.34-(d, 1H J=4.1 Hz), 7.24 (s, 1H); $^{13}$C NMR (CDCl$_3$) δ7.4, 28.4, 60.2, 67.2, 71.0, 127.6, 132.1, 159.7, 165.7; IR (NaCl) 3229, 3015, 2969, 1753 cm$^{-1}$; MS m/z 199.

1.0 gram (0.005 mole) of the 4-(acryloxymethyl)-4-ethyl-2-oxazolidinone prepared as described above, 1.1 grams (0.01 mole) tertiary butyl hypochlorite, and 5.0 milliliters methylene chloride were added to a one-neck round bottom flask. The solution was stirred at room temperature for 30 minutes and the solvent removed under reduced pressure. 1.17 grams (100% of the yield theoretically expected) 3-chloro-4-(acryloxymethyl)-4-ethyl-2-oxazolidinone(1a-Cl) was obtained as a clear oil. The product had the following spectral data: $^1$H NMR (CDCl$_3$) δ0.93(t, 3H J=1.8 Hz), 1.54–1.78(m, 2H), 4.10–4.23 (m, 4H), 5.84-(d, 1H J=2.4 Hz), 5.98–6.10(m, 1H), 6.32(d, 1H J=4.2 Hz); $^{13}$C NMR (CDCl$_3$) δ6.6, 24.7, 65.9, 67.7, 71.0, 127.2, 132.6, 159.6, 165.3; IR (NaCl) 2969, 1783 cm$^{-1}$; MS m/z 234.

1.0 gram (0.005 mol) of the 4-(acryloxymethyl)-4-ethyl-2-oxazolidinone prepared as described above, and 50 milliliters of a 0.1 normal sodium hypobromite solution were stirred together at room temperature for 30 minutes in a sealed flask. The solution was then extracted with three 50 milliliter portions of methylene chloride, and the organic layer was washed with saturated sodium chloride solution and dried over sodium sulfate. The solvent was removed under reduced pressure to give 1.40 grams (100% of the yield theoretically expected) 3-bromo-4-(acryloxymethyl)-4-ethyl-2-oxazolidinone(1a-Br) as a clear oil. The product exhibited the following spectral data: $^1$H NMR (CDCl$_3$) δ0.90(t, 3H J=2.0 Hz), 1.58–1.81(m, 2H), 4.15–4.27(m, 4H), 5.80(d, 1H J=2.3 Hz), 6.00–6.15(m, 1H), 6.37(d, 1H J=4.5 Hz); $^{13}$C NMR (CDCl$_3$) δ7.6, 25.6, 64.9, 68.3, 71.7, 123.2, 136.6, 159.1, 165.5; IR (NaCl) 2970, 1775 cm$^{-1}$; MS m/z 278.

Example 2

Preparation of 4-(crotonoxymethyl)-4-ethyl-2-oxazolidinone(1b)

3.1 grams (0.021 mole) 4-ethyl-4-hydroxymethyl-2-oxazolidinone, prepared identically to that discussed in example 1, 2.3 grams (0.022 mole) trans-crotonyl chloride, and 25 milliliters chloroform were mixed in a one-necked round-bottom flask. The procedure employed was identical to that discussed in example 1. 4.20 grams (98% of the yield theoretically expected) of pure product was obtained as a clear oil. The product exhibited the following spectral data: $^1$H NMR (CDCl$^3$) δ0.90(t, 3H J=1.8 Hz), 1.48–1.67 (m, 2H), 1.83(d, 3H J=3.6 Hz), 3.97–4.19 (m, 4H), 5.79(d, I H J=3.6 Hz), 6.90–6.99(m, 2H); $^{13}$C NMR (CDCl$_3$) δ7.3, 18.1, 28.3, 60.2, 66.7, 70.9, 121.7, 146.3, 159.6, 166.0; IR (NaCl) 3229, 3020, 2960, 1780 cm$^{-1}$; MS m/z 213. This monomer can be chlorinated or brominated by the same procedure as in example 1.

Example 3

Preparation of 4-(2'-methylacryloxymethyl)-4-ethyl-2-oxazolidinone (1c)

3.1 grams (0.021 mole) 4-ethyl-4-hydroxymethyl-2-oxazolidinone, prepared identically to that discussed in example 1, 2.3 grams (0.022 mole) 2-methylacryloyl chloride, and 25 milliliters chloroform were mixed in a one-necked round-bottom flask. The procedure employed was identical to that discussed in example 1. 2.56 grams (60% the yield theoretically expected) of pure product was obtained as a brown oil. The product gave the following spectral data: $^1$H NMR (CDCl$_3$) δ0.92(t, 3H J=1.8 Hz), 1.46–1.65(m, 2H), 1.93(s, 3H), 4.12–4.25(m, 4H), 5.55(s, 1H), 6,07(s, 1H), 7.06 (s, 1H); $^{13}$C NMR (CDCl$_3$) δ7.2, 18.0, 27.7, 60.2, 65.6, 70.8, 126.6, 135.4, 160.4, 166.8; IR (NaCl) 3230, 3010, 2960, 1740 cm$^{-1}$, MS m/z 213. This monomer can be chlorinated or brominated by the same procedure as in example 1.

Example 4

Preparation of 4-(3',3'-dimethylacryloxymethyl)-4-ethyl-2-oxazolidinone (1d)

3.1 grams (0.021 mole) 4-ethyl-4-hydroxymethyl-2-oxazolidinone, prepared identically to that discussed in example 1, 2.6 grams (0.022 mole) 3,3-dimethylacryloyl chloride, and 25 milliliters chloroform were mixed in a one-necked round-bottom flask. The procedure employed was identical to that discussed in example 4. 4.10 grams (90% of the yield theoretically expected) of pure product was obtained as a yellow oil. The product exhibited the following spectral data: $^1$H NMR (CDCl$_3$) δ0.98(t, 3H J=1.2 Hz), 1.65–1.71(m, 2H), 1.92(s, 3H), 2.17(s, 3H), 4.04–4.23 (m. 4H), 5.71(s, 1H), 6.43(s, 1H); $^{13}$C NMR (CDCl$_3$) δ7.6, 20.6, 27.7, 28.7, 60.3, 66.1, 71.3, 115.2, 159.0, 159.5, 166.2; IR (NaCl) 3215, 3020, 2970, 1785 cm$^{-1}$; MS m/z 227. This monomer can be chlorinated or brominated by the same procedure as in example 1.

Example 5

Preparation of poly-3-chloro-4-(acryloxymethyl)-4-ethyl-2-oxazolidinone (2a)

1.0 gram (0.005 mole) 4-(acryloxymethyl)-4-ethyl-2-oxazolidinone, prepared identically to that discussed in example 1, 0.01 grams (6.1×10$^{-5}$ mole) 2,2'-azobisisobutyronitrile, and 10 milliliters anhydrous N,N-dimethylformamide were added to a two-neck round-bottom flask. The reagents were purged with nitrogen for fifteen minutes, and the flask was sealed and heated to 70° C. for ten hours with stirring. The viscous solution was cooled to room temperature and was drop-added into 200 milliliters water. The polymer immediately precipitated out and was filtered and dried in a vacuum oven to give 0.9 grams (90% of the yield theoretically expected) pure product as an amorphous solid. The product, poly-4-(acryloxymethyl)-4-ethyl-2-oxazolidinone, exhibited the following spectral data: $^{13}$C NMR (CDCl$_3$) δ7.1, 27.6, 30.8, 35.7, 59.2, 60.9, 67.1, 69.8, 158.1, 162.3; IR (neat) 3400, 2937, 1757 cm$^{-1}$.

0.5 grams (0.0025 mole) poly-4-(acryloxymethyl)-4-ethyl-2-oxazolidinone, prepared identically to that discussed above, 0.3 grams (0.0028 mole) tertiary butyl hypochlorite, and 10 milliliters methylene chloride were added to a one-neck round bottom flask. The reagents were stirred vigorously for 30 minutes and the solvent removed under reduced pressure. The residue was dried in a vacuum oven to give 0.58 grams (100% of the yield theoretically expected) poly-3-chloro-4-(acryloxymethyl)-4-ethyl-2-oxazolidinone (2a) as an amorphous solid. The product exhibited the following spectral data: $^{13}C$ NMR (CDCl$^3$) δ7.5, 26.6, 31.8, 35.7, 59.2, 60.3, 69.1, 70.0, 159.1, 160.3; IR (neat) 3400, 2937, 1780 cm$^{-1}$. This polymer can be brominated by the same procedure as employed in example 6.

Example 6

Preparation of poly-acrylonitrile-co-3-halo-4-(acryloxymethyl)-4-ethyl-2-oxazolidinone (3a-Cl, 3a-Br)

1.0 gram (0.005 mole) 4-(acryloxymethyl)-4-ethyl-2-oxazolidinone, prepared identically to that discussed in example 1, 2.7 grams (0.05 mole) acrylonitrile (Aldrich Chemical Co. Milwaukee, Wis.), 0.02 grams ($1.2 \times 10^{-6}$ mole) 2,2'-azobisisobutyronitrile, and 10 milliliters anhydrous N,N-dimethylformamide were placed in a two-neck round-bottom flask. The reaction mixture was purged with nitrogen for fifteen minutes and the flask sealed and heated to 70° C. for 10 hours with stirring. The solution was cooled to room temperature and the polymer precipitated in 200 milliliters water. The polymer was filtered off, redissolved in N,N-dimethylformamide, and reprecipitated two more times. The resulting solid was filtered and dried in a vacuum oven to give 3.3 g (90% of the yield theoretically expected) pure product as a white solid. The product, poly-acrylonitrile-co-4-(acryloxymethyl)-4-ethyl-2-oxazolidinone, exhibited the following spectral data: $^{13}C$ NMR (DMSO-d$_6$) δ7.17, 26.7, 27.4, 27.9, 30.6, 32.6, 35.7, 59.2, 67.7, 69.9, 116.6, 120.0, 120.3, 158.2, 162.3; IR (KBr) 3400, 2938, 2244, 1757 cm$^{-1}$.

1.0 gram of poly-acrylonitrile-co-4-(acryloxymethyl)-4-ethyl-2-oxazolidinone, prepared identically as that discussed above and 50 milliliters 2.0 normal sodium hydroxide were added to an Erlenmeyer flask. The stirred, heterogeneous solution was cooled in an ice bath until the temperature was 10° C. Chlorine gas (Matheson Gas Co., Montgomeryville, Pa.) was bubbled into the solution slowly so the temperature did not exceed 15° C. Once the pH reached 7.0, the chlorine gas flow was stopped, and the flask was sealed for thirty minutes. The solution was allowed to come to room temperature and was vacuum filtered. The resulting solid was washed with 200 milliliters distilled water and was dried to give 1.0 gram (90% of the yield theoretically expected) poly-acrylonitrile-co-3-chloro-4-(acryloxymethyl)-4-ethyl-2-oxazolidinone (3a-Cl) as a white solid. The product exhibited the following spectral data: IR (KBr) 2940, 2243, 1764 cm$^{-1}$. Comparable results were obtained using compounds 1b–1d.

1.0 gram of poly-acrylonitrile-co-4-(acryloxymethyl)-4-ethyl-2-oxazolidinone, prepared identically as that discussed above, and 50 milliliters 0.1 normal sodium hypobromite were stirred at room temperature for 30 minutes in a sealed flask. The solution was then filtered and the solid washed with 200 milliliters distilled water and dried to give 1.0 gram poly-acrylonitrile-co-3-bromo-4-(acryloxymethyl)-4-ethyl-2-oxazolidinone (3a-Br) as a pale yellow solid. The product exhibited the following spectral data: IR (KBr) 2950, 2245, 1770 cm$^{-1}$. Comparable results were obtained using compounds 1b–1d.

Example 7

Preparation of poly-styrene-co-3-chloro-4-(acryloxymethyl)-4-ethyl-2-oxazolidinone (3b)

A copolymerization was performed with 4-(acryloxymethyl)-4-ethyl-2-oxazolidinone and styrene (Aldrich Chemical Co., Milwaukee, Wis.) using the procedure employed which was identical to that discussed in example 6. The yield of poly-styrene-co-4-(acryloxymethyl)-4-ethyl-2-oxazolidinone was 90% of that theoretically expected. The product exhibited prominent infrared bands in a KBr pellet at 2930 and 1754 cm$^{-1}$.

Chlorination of the above sample in the manner analogous to that discussed in example 6 produced poly-styrene-co-3-chloro-4-(acryloxymethyl)-4-ethyl-2-oxazolidinone (3b) in 100% yield with prominent infrared bands in a KBr pellet at 2927 and 1767 cm$^{-1}$. Comparable results were obtained with compounds 1b–1d, and the bromination can be done in the manner described in example 6.

Example 8

Preparation of poly-vinyl chloride-co-3-chloro-4-(acryloxymethyl)-4-ethyl-2-oxazolidinone (3c)

A copolymerization was performed with 4-(acryloxymethyl)-4-ethyl-2-oxazolidinone and vinyl chloride (Aldrich Chemical Co., Milwaukee, Wis.) using the procedure employed which was identical to that discussed in example 6. The yield of poly-vinyl chloride-co-4-(acryloxymethyl)-4-ethyl-2-oxazolidinone was 90% of that theoretically expected. The product exhibited prominent infrared bands in a KBr pellet at 2920 and 1750 cm$^{-1}$.

Chlorination of the above sample in the manner analogous to that discussed in example 6 produced poly-vinyl chloride-co-3-chloro-4-(acryloxymethyl)-4-ethyl-2-oxazolidinone (3c) in 100% yield with prominent infrared bands in a KBr pellet at 2930 and 1770 cm$^{-1}$. Comparable results were obtained with compounds 1b–1d, and the bromination can be done in the manner described in example 6.

Example 9

Preparation of poly-acrylonitrile-co-4-(acryloxymethyl)-4-ethyl-2-oxazolidinone latex (3d)

5.0 grams (0.025 mole) 4-(acryloxymethyl)-4-ethyl-2-oxazolidinone, prepared identically to that discussed in example 1, 10.0 grams (0.190 mole) acrylonitrile, 30.0 grams (1.67 mole) water, and 0.20 grams ($6.94 \times 10^{-4}$ mole) sodium lauryl sulfate were added to a three-necked round-bottom flask equipped with a gas inlet and reflux condenser. The solution was stirred and heated to 60° C. and purged with nitrogen for ten minutes. A solution of 0.025 grams ($9.26 \times 10^{-5}$ mole) potassium persulfate and 1.0 milliliter water was prepared and added in the reaction mixture after the nitrogen purge was completed. The reaction was stirred for twelve hours and then cooled to room temperature. Any precipitated polymer was allowed to settle, and the latex was decanted off. The product poly-acrylonitrile-co-4-(acryloxymethyl)-4-ethyl-2-oxazolidinone latex (3d) was produced in 95% yield with prominent infrared bands in a KBr pellet at 2985, 2244, and 1750 cm$^{-1}$. Comparable results were obtained with compounds 1b–1d, and the bromination can be done in the manner described in example 6.

Example 10

Preparation of poly-vinyl chloride-co-4-(acryloxymethyl)-4-ethyl-2-oxazolidinone latex (3e)

An emulsion copolymerization was performed with 4-(acryloxymethyl)-4-ethyl-2-oxazolidinone and vinyl chloride using the procedure employed which was identical to that discussed in example 9. The yield of poly-vinyl chloride-co-4-(acryloxymethyl)-4-ethyl-2-oxazolidinone latex (3e) was 90% of that theoretically expected. The product exhibited prominent infrared bands in a KBr pellet at 2980 and 1750 cm$^{-1}$. Comparable results were obtained with compounds 1b–1d, and the bromination can be done in the manner described in example 6.

Example 11

Preparation of poly-styrene-co-4-(acryloxymethyl)-4-ethyl-2-oxazolidinone latex (3f)

An emulsion copolymerization was performed with 4-(acryloxymethyl)-4-ethyl-2-oxazolidinone and styrene using the procedure employed which was identical to that discussed in example 9. The yield of poly-styrene-co-4-(acryloxymethyl)-4-ethyl-2-oxazolidinone latex (3f) was 90% of that theoretically expected. The product exhibited prominent infrared bands in a KBr pellet at 3050, 2985, and 1750 cm$^{-1}$. Comparable results were obtained with compounds 1b–1d, and the bromination can be done in the manner described in example 6.

Example 12

Preparation of poly-vinyl acetate-co-4-(acryloxymethyl)-4-ethyl-2-oxazolidinone latex (3g)

An emulsion copolymerization was performed with 4-(acryloxymethyl)-4-ethyl-2-oxazolidinone and vinyl acetate (Aldrich Chemical Co., Milwaukee, Wis.) using the procedure employed which was identical to that discussed in example 9. The yield of poly-vinyl acetate-co-4-(acryloxymethyl)-4-ethyl-2-oxazolidinone latex (3g) was 90% of that theoretically expected. The product exhibited prominent infrared bands in a KBr pellet at 2985, 1772, and 1750 cm$^{-1}$. Comparable results were obtained with compounds 1b–1d, and the bromination can be done in the manner described in example 6.

Example 13

Preparation of poly-acrylonitrile-g-3-chloro-4-(acryloxymethyl)-4-ethyl-2-oxazolidinone (4a)

2.3 grams (0.013 mole) 4-(acryloxymethyl)-4-ethyl-2-oxazolidinone, prepared identically to that discussed in example 1, 10 grams poly-acrylonitrile latex which was prepared from acrylonitrile using the method described by Hayes, R. A., *J. Polymer Sci.*, 11:531 (1967), and 20 grams (1.1 mole) water, were added to a 100 milliliters three-neck round bottom flask. The reagents were purged with nitrogen for fifteen minutes; the flask was then sealed and heated to 60° C. with stirring. Once the internal temperature reached 60° C., 0.05 grams (1.9×10$^{-4}$ mole) potassium persulfate, dissolved in 1.0 milliliters water, was added in to the reaction mixture. The reaction mixture was heated and stirred for twelve hours, then cooled to room temperature. The polymer was precipitated into 150 milliliters of a saturated sodium chloride solution to give a white solid. The solid was collected by vacuum filtration and extracted with 200 milliliters boiling 50/50 DMF/water. The resulting solid was refiltered and re-extracted two more times to give 5.0 grams poly-acrylonitrile-g-4-(acryloxymethyl)-4-ethyl-2-oxazolidinone in 75% yield with prominent infrared bands in a KBr pellet at 2965, 2240, and 1750 cm$^{-1}$.

2.0 grams of the poly-acrylonitrile grafted copolymer product prepared as described above and 50 milliliters 2.0 normal sodium hydroxide were placed in an Erlenmeyer flask in an ice bath with stirring. The stirred mixture was maintained at a temperature lower than 10° C., while chlorine gas was bubbled in until the pH reached 7.0, at which time the flask was sealed and stirred for thirty minutes at room temperature. The solution was filtered, washed with 200 milliliters water, and dried to give 2.0 grams poly-acrylonitrile-g-3-chloro-4-(acryloxymethyl)-4-ethyl-2-oxazolidinone (4a) in 100% yield with prominent infrared bands in a KBr pellet at 2960, 2240, and 1768 cm$^{-1}$. Comparable results were obtained with compounds 1b–1d, and the bromination can be done in the manner described in example 6.

Example 14

Preparation of poly-styrene-g-3-chloro-4-(acryloxymethyl)-4-ethyl-2-oxazolidinone (4b)

A grafting copolymerization was performed with 4-(acryloxymethyl)-4-ethyl-2-oxazolidinone and poly-styrene using the procedure employed which was identical to that discussed in example 13. The yield of poly-styrene-g-4-(acryloxymethyl)-4-ethyl-2-oxazolidinone was 85% of that theoretically expected, and the product exhibited prominent infrared bands in a KBr pellet at 3015, 2980, and 1747 cm$^{-1}$.

The poly-styrene grafted copolymer was then chlorinated in a manner analogous to that discussed in example 13 and produced poly-styrene-g-3-chloro-4-acryloxymethyl-4-ethyl-2-oxazolidinone (4b) in 100% yield with prominent infrared bands in a KBr pellet at 3020, 2985, and 1765 cm$^{-1}$. Comparable results were obtained with compounds 1b–1d, and the bromination can be done in the manner described in example 6.

Example 15

Preparation of poly-vinyl alcohol-g-3-chloro-4-(acryloxymethyl)-4-ethyl-2-oxazolidinone (4c)

A grafting copolymerization was performed with 4-(acryloxymethyl)-4-ethyl-2-oxazolidinone and poly-vinyl alcohol using the procedure employed which was identical to that discussed in example 13. The yield of poly-vinyl alcohol-g-4-(acryloxymethyl)-4-ethyl-2-oxazolidinone was 95% of that theoretically expected, and the product exhibited prominent infrared bands in a KBr pellet at 3415, 2975, and 1757 cm$^{-1}$.

The poly-vinyl alcohol grafted copolymer was then chlorinated in a manner analogous to that discussed in example 13 and produced poly-vinyl alcohol-g-3-chloro-4-acryloxymethyl-4-ethyl-2-oxazolidinone (4c) in 100% yield with prominent infrared bands in a KBr pellet at 3420, 2980, and 1760 cm$^{-1}$. Comparable results were obtained with compounds 1b–1d, and the bromination can be done in the manner described in example 6.

Example 16

Preparation of poly-vinyl acetate-g-3-chloro-4-(acryloxymethyl)-4-ethyl-2-oxazolidinone (4d)

A grafting copolymerization was performed with 4-(acryloxymethyl)-4-ethyl-2-oxazolidinone and poly-vinyl acetate using the procedure employed which was identical to that discussed in example 13. The yield of poly-vinyl acetate-g-4-(acryloxymethyl)-4-ethyl-2-oxazolidinone was 90% of that theoretically expected, and the product exhibited prominent infrared bands in a KBr pellet at 2980, 1750, and 1710 cm$^{-1}$.

The poly-vinyl acetate grafted copolymer was then chlorinated in a manner analogous to that discussed in example 13 produced poly-vinyl acetate-g-3-chloro-4-acryloxymethyl-4-ethyl-2-oxazolidinone (4d) in 100% yield with prominent infrared bands in a KBr pellet at 2980, 1768, and 1710 cm$^{-1}$. Comparable results were obtained with compounds 1b–1d, and the bromination can be done in the manner described in example 6.

Example 17

Preparation of poly-vinyl chloride-g-3-chloro-4-(acryloxymethyl)-4-ethyl-2-oxazolidinone (4e)

A grafting copolymerization was performed with 4-(acryloxymethyl)-4-ethyl-2-oxazolidinone and poly-vinyl chloride using the procedure employed which was identical to that discussed in example 13. The yield of poly-vinyl chloride-g-4-(acryloxymethyl)-4-ethyl-2-oxazolidinone was 75% of that theoretically expected, and the product exhibited prominent infrared bands in a KBr pellet at 2975 and 1740 cm$^{-1}$.

The poly-vinyl chloride grafted copolymer was then chlorinated in a manner analogous to that discussed in example 13 produced poly-vinyl chloride-g-3-chloro-4-acryloxymethyl-4-ethyl-2-oxazolidinone (4e) in 100% yield with prominent infrared bands in a KBr pellet at 2970 and 1767 cm$^{-1}$. Comparable results were obtained with compounds 1b–1d, and the bromination can be done in the manner described in example 6.

Example 18

Preparation of cellulose-g-3-chloro-4-(acryloxymethyl)-4-ethyl-2-oxazolidinone (4f)

1.0 gram cellulose and 50.0 milliliters 0.05 normal nitric acid were placed in an Erlenmeyer flask and stirred for 30 minutes at 30° C. under nitrogen. 1.54 grams (0.008 mole) 4-(acryloxymethyl)-4-ethyl-4-hydroxymethyl-2-oxazolidinone, prepared identically to that discussed in example 1, was added, and the reaction was stirred for 15 minutes; then 0.11 grams (2.0×10$^{-4}$ mole) ceric ammonium nitrate was added to the reaction. A continuous supply of purified nitrogen was maintained throughout the reaction period of 30 minutes, at which time the polymerization was complete and the cellulose filtered off. The solid was washed with distilled water and acetone and dried in an oven at 50° C. to give cellulose-g-3-4-(acryloxymethyl)-4-ethyl-2-oxazolidinone in 100% yield.

The grafted cellulose, as described above, was chlorinated by soaking it in a diluted sodium hypochlorite solution for 20 minutes, washed with synthetic chlorine-demand-free water, and dried at room temperature overnight to produce, cellulose-g-3-chloro-4-(acryloxymethyl)-4-ethyl-2-oxazolidinone (4f).

Example 19

Efficacies of the Poly N-halamine Compounds Against *Staphylococcus aureus*

Solid samples of the poly N-halamine compounds described in examples 6–18 were packed into glass Pasteur pipettes (5.75 inches long, 0.25 inches inside diameter) at a length of 1.0 inch. The samples were washed with pH 7.0 aqueous solution and then 10$^6$ CFU per milliliter of *Staphylococcus aureus* (ATCC 6538) was added to the pipette, and the inoculum was allowed to pass through the packed column using gravity feed in most cases. The particle size for some of the polymer samples was sufficiently small that compressed nitrogen was used to force the inoculum through the column to enhance flow rates. The effluent from each sample was collected, and 25 microliter aliquots were removed and plated on nutrient agar. The remaining portions of the effluents were recycled through the columns. This procedure was repeated 5–6 times which allowed for an assessment of biocidal contact times. The plated samples were incubated at 37° C. for 48 hours and then examined for viable growth. Control samples consisted of plating aliquots of the bacterial suspension before passing the bacteria through the biocidal polymer columns, or in some cases, of passing the bacteria through columns containing unchlorinated precursor polymer samples having similar particle sizes. In all cases the two types of control experiments yielded plates which contained confluent growth too numerous to count indicating that the bacterial samples were viable and that the organisms were not simply eliminated by filtration upon passing through the samples. Results are tabulated in Table I.

The data in Table I demonstrate that all of the N-halamine biocidal polymers tested were effective at inactivating *S. aureus* over extended periods of time.

TABLE I

Biocidal Effects of the N-halamine Polymers

| Polymer[a] | Mesh Size | Column Length (inches) | Age (Days)[b] | Contact Time for 6-log Inactivation of *S. aureus* (min) |
|---|---|---|---|---|
| 3a-Cl | >45 | 1.0 | 3 | ≦2.28 |
| 3a-Cl | >45 | 1.0 | 365 | 4.56–5.30 |
| 3a-Br | >45 | 1.0 | 1 | ≦1.30 |
| 3b | 35-60 | 1.0 | 4 | ≦1.35 |
| 3b | 35-60 | 1.0 | 365 | 2.35–3.02 |
| 3c | 35-60 | 1.0 | 2 | ≦1.25 |
| 3c | 35-60 | 1.0 | 365 | 1.96–2.35 |
| 4a | 35-60 | 1.0 | 5 | ≦2.65 |
| 4a | 35-60 | 1.0 | 60 | ≦3.56 |
| 4b | 35-60 | 1.0 | 10 | ≦1.25 |
| 4b | 35-60 | 1.0 | 65 | ≦1.30 |
| 4e | 35-60 | 1.0 | 5 | ≦1.05 |
| 4e | 35-60 | 1.0 | 68 | ≦1.25 |

[a]3a-Cl = poly-acrylonitrile-co-3-chloro-4-(acryloxymethyl)-4-ethyl-2-oxazolidinone
3a-Br = poly-acrylonitrile-co-3-chloro-4-(acryloxymethyl)-4-ethyl-2-oxazolidinone
3b = poly-styrene-co-3-chloro-4-(acryloxymethyl)-4-ethyl-2-oxazolidinone
3c = poly-vinyl chloride-co-3-chloro-4-(acryloxymethyl)-4-ethyl-2-oxazolidinone
4a = poly-acrylonitrile-g-3-chloro-4-(acryloxymethyl)-4-ethyl-2-oxazolidinone
4b = poly-styrene-g-3-chloro-4-(acryloxymethyl)-4-ethyl-2-oxazolidinone
4e = poly-vinyl chloride-g-3-chloro-4-(acryloxymethyl)-4-ethyl-2-oxazolidinone
[b]Time in days elapsing between sample synthesis and biocidal test run with storage at room temperature.

Example 20

Efficacies of N-Halamine Compounds Against *Staphylococcus aureus* in Aqueous Solution The bacterial efficacies of the compounds against *S. aureus* (ATCC 6538) in chlorine-demand-free water were determine by using techniques employed previously in extensive detail by Williams et al., *Appl. Environ. Microbial.*, 54:2583 (1987). Solutions containing 10$^6$ CFU final cell densities of bacteria were prepared and treated with the various disinfectant compounds described in examples 1–17 at either 5 or 10 milligrams/liter total chlorine concentration which was previously determined by titration using a stock solution with sodium thiosulfate. Aliquots were removed at several predetermined times, and the active halogen was quenched by sterile 0.02 normal sodium thiosulfate. Serial dilutions were made into sterile saline, and three 25 microliter aliquots of each dilution were applied to the dried surface of a Petri dish containing nutrient agar. After incubation at 37° C. for 48 hours, the three replicates for each dilution were counted and averaged. Control samples containing no disinfectant, or in some cases, unchlorinated precursor compounds, were handled in the same manner. In all cases the two types of control experiments yielded plates which contained confluent growth too numerous to count indicating that the bacterial samples were viable. Inactivation of the organism was considered to be at least 99.9999% when no colonies were detected in the thiosulfate-quenched aliquots.

The data in Table II demonstrate that all of the soluble N-halamine biocidal compounds tested were effective at inactivating *S. aureus* in less than 10 minutes.

TABLE II

Biocidal Effects of the N-Halamine Compounds

| Compound[a] | pH | Temperature (° C.) | Contact Time for 6-log Inactivation of *S. aureus* (min). |
|---|---|---|---|
| 1a-Cl | 7.0 | 22 | <5 |
| 1a-Br | 7.0 | 22 | <5 |
| 2a | 7.0 | 22 | <5 |
| 3g | 7.0 | 22 | 5–10 |
| 4c | 7.0 | 22 | 5–10 |
| 4d | 7.0 | 22 | 5–10 |

[a]1a-Cl = 3-chloro-4-(acryloxymethyl)-4-ethyl-2-oxazolidinone
1a-Br = 3-bromo-4-(acryloxymethyl)-4-ethyl-2-oxazolidinone
2a = poly-3-chloro-4-(acryloxymethyl)-4-ethyl-2-oxazolidinone
3g = poly-vinyl acetate-co-3-chloro-4-(acryloxymethyl)-4-ethyl-2-oxazolidinone latex
4c = poly-vinyl alcohol-g-3-chloro-4-(acryloxymethyl)-4-ethyl-2-oxazolidinone
4d = poly-vinyl acetate-g-3-chloro-4-(acryloxymethyl)-4-ethyl-2-oxazolidinone Example 21

Preparation of Surface Films and Coatings

Unchlorinated poly N-halamine compounds described in examples 5–17 were cast into thin films on various surfaces and then chlorinated to determine the biocidal efficacy of these disinfectant surfaces. The general method for coating granular polymeric materials on to various substrates is as follows. 1.0 gram of the unchlorinated polymer was dissolved in 50 milliliters of an appropriate solvent and the solution filtered to remove any undissolved polymer particles. The substrate to be coated was washed, autoclaved, and dried at 100° C. before the polymer solution was added. Enough of the polymeric solution was added to coat the surface of the substrate without running over the sides; then the material with the polymer solution coating it was heated in an oven set between 80–100° C. until the solvent was removed. In all cases, the coating was clear, tough, resistant to abrasion, and had good adherence to the substrate. Once coated, the surface was chlorinated with a diluted solution of sodium hypochlorite (3000 ppm free chlorine) by soaking the surface in the aqueous solution for 20 minutes. The surface was then removed, washed with synthetic chlorine-demand-free water, and dried at room temperature overnight to ensure all residual sodium hypochlorite was removed.

For the case in which an emulsion or latex was used, the emulsified solution was added directly to the substrate, prepared in the same manner as described above, and heated to remove the solvent, water, as well as coalesce the polymer particles to form the coating. The chlorination of the coating was done in the same manner as described above.

Example 22

Efficacies of Poly N-Halamine Surfaces Against *Staphylococcus aureus*

The surfaces to be tested for biocidal activity against *S. aureus* (ATCC 6538) were applied to a circular glass coverslip measuring 12 millimeters in diameter. The surfaces were chlorinated in the same manner as mentioned in example 21. 50 microliters of a $10^6$ CFU solution of *S. aureus* were placed on the surface, and a 25 microliter aliquot was removed at a predetermined time, and the active halogen was quenched by sterile 0.02 normal sodium thiosulfate. The aliquot was then applied to the dried surface of a Petri dish containing nutrient agar. After incubation at 37° C. for 48 hours, the bacteria were counted. Control samples containing no disinfectant, or in some cases, unchlorinated precursor surfaces, were handled in the same manner. In all cases the two types of control experiments yielded plates which contained confluent growth too numerous to count indicating that the bacterial samples were viable. Inactivation of the organism was considered to be at least 99.9999% when no colonies were detected in the thiosulfate-quenched aliquots.

The data in Table III demonstrate that all of the N-halamine biocidal compounds tested were effective at inactivating *S. aureus* on a glass surface.

TABLE III

Biocidal Effects of the N-Halamine Surfaces

| Compound[a] | Chlorination Time (min) | Age (Days)[b] | Contact Time for 6-log Inactivation of *S. aureus* (min) |
|---|---|---|---|
| 3d | 20 | 5 | 10–20 |
| 3g | 10 | 12 | 5–10 |
| 4c | 20 | 60 | 5–10 |
| 4d | 10 | 20 | 5–10 |
| 4e | 30 | 3 | 30–60 |

[a]3d = poly-acrylonitrile-co-3-chloro-4-(acryloxymethyl)-4-ethyl-2-oxazolidinone latex
3g = poly-vinyl acetate-co-3-chloro-4-(acryloxymethyl)-4-ethyl-2-oxazolidinone latex
4c = poly-vinyl alcohol-g-3-chloro-4-(acryloxymethyl)-4-ethyl-2-oxazolidinone
4d = poly-vinyl acetate-g-3-chloro-4-(acryloxymethyl)-4-ethyl-2-oxazolidinone
4e = poly-vinyl chloride-g-3-chloro-4-(acryloxymethyl)-4-ethyl-2-oxazolidinone
[b]Time in days elapsing between sample synthesis and biocidal test run with storage at room temperature.

Example 23

Poly N-Halamine Zone of Inhibition Studies for Fabrics

Zone of inhibition studies were performed for fabric materials coated with various poly N-halamines described in examples 9–18 with the coating and chlorination protocol used in example 21. The coated fabric samples were cut into 1–1.5 cm squares prior to chlorination and dried thoroughly after chlorination, and they were placed on a Tryptic Soy agar plate which was inoculated with *Staphylococcus aureus*

(ATCC 6538). The plates were incubated for 24 hours at 37° C. The zones of inhibition were measured, and the results are tabulated in Table IV. The bacteria were not able to colonize on the fabric samples, and small zones of inhibition were produced around them.

TABLE IV

Zones of Inhibition of Poly N-Halamines

| Polymer[a] | Fabric Material[b] | % Weight Increase | Zone in mm[c] |
|---|---|---|---|
| 3d | Printcloth | 15.6 | 0.5 |
| 3d | Cotton | 20.3 | 1.0 |
| 3e | Printcloth | 25.1 | 0.1 |
| 3e | Cotton | 30.3 | 0.2 |
| 3f | Printcloth | 30.1 | 0.5 |
| 3g | Printcloth | 23.2 | 0.5 |
| 4a | Printcloth | 19.5 | 0.8 |
| 4a | Cotton | 26.2 | 1.2 |
| 4b | Printcloth | 13.5 | 0.3 |
| 4c | Printcloth | 30.2 | 0.5 |
| 4c | Cotton | 36.1 | 1.0 |
| 4e | Printcloth | 15.7 | 0.1 |
| 4e | Cotton | 20.6 | 0.1 |

3d = poly-acrylonitrile-co-3-chloro-4-(acryloxymethyl)-4-ethyl-2-oxazolidinone latex
3e = poly-vinyl chloride-co-3-chloro-4-(acryloxymethyl)-4-ethyl-2-oxazolidinone latex
3f = poly-styrene-co-3-chloro-4-(acryloxymethyl)-4-ethyl-2-oxazolidinone latex
3g = poly-vinyl acetate-co-3-chloro-4-(acryloxymethyl)-4-ethyl-2-oxazolidinone latex
4a = poly-acrylonitrile-g-3-chloro-4-(acryloxymethyl)-4-ethyl-2-oxazolidinone
4b = poly-styrene-g-3-chloro-4-(acryloxymethyl)-4-ethyl-2-oxazolidinone
4c = poly-vinyl alcohol-g-3-chloro-4-(acryloxymethyl)-4-ethyl-2-oxazolidinone
4e = poly-vinyl chloride-g-3 chloro-4-(acryloxymethyl)-4-ethyl-2-oxazolidinone
[b]Printcloth comprises a 54/46 cotton/polyester blend.
[c]Length in mm from the edge of the fabric to the viable bacteria.

Example 24

Efficacies of Poly N-Halamines on Fabric Against Salmonella enteritidis

Fabric materials coated with various poly N-halamines described in examples 9–18 containing the coating and chlorination protocol used in example 21 were challenged with the bacterium Salmonella enteritidis according to protocol #100 of the American Association of Textile Chemists and Colorants (AATCC), slightly modified to accommodate small sample size. In this test procedure, each fabric sample was prepared as a disc of diameter 1.0 centimeter and challenged with 100 microliters of a suspension containing $10^6$ colony forming units (CFU) of the bacteria for a contact time of 10 minutes at ambient temperature. Control samples coated with unchlorinated polymers were similarly challenged. At the end of the incubation period each sample was immersed in 10 milliliters of 0.02 normal sodium thiosulfate solution in a 50 milliliter test tube to quench chlorine biocidal action and was agitated vigorously for 60 seconds. Aliquots of 100 microliters were removed from the tubes, serially diluted in sterile water, and plated in duplicate on 10 centimeter diameter Trypticase-Soy agar plates for 24 hours at 37° C. The numbers of colony forming units of surviving bacteria present in the eluates were determined, and compared to the total numbers detected in the eluates from the corresponding challenged control samples, to establish the percent reduction brought about by each of the chlorinated polymers. The data are tabulated in Table V. The three polymer coatings tested were clearly effective at significantly reducing the numbers of CFU of Salmonella enteritidis over a 10 minute contact period.

TABLE V

Reduction of S. enteritidis Caused by Poly N-Halamines on Fabric

| Polymer[a] | Fabric Material[b] | % Dry Weight Gain on Fabric | % Reduction of enteritidis in 10 min. |
|---|---|---|---|
| 3d | Printcloth | 20.3 | 97.0 |
| 3g | Printcloth | 18.5 | 99.99 |
| 4c | Printcloth | 22.3 | 99.9 |

3d = poly-acrylonitrile-co-3-chloro-4-(acryloxymethyl)-4-ethyl-2-oxazolidinone latex
3g = poly-vinyl acetate-co-3-chloro-4-(acryloxymethyl)-4-ethyl-2-oxazolidinone latex
4c = poly-vinyl alcohol-g-3-chloro-4-(acryloxymethyl)-4-ethyl-2-oxazolidinone
[b]printcloth comprises a 54/46 cotton/polyester blend.

Example 25

Efficacies of Poly N-Halamine Coatings Against Pseudomonas aeruginosa in Flowing Water N-halamine polymers 3 g (poly-vinyl acetate-co-3-chloro4-(acryloxymethyl)-4-ethyl-2-oxazolidinone latex) and 4e (poly-vinyl chloride-g-3-chloro-4-(acryloxymethyl)-4-ethyl-2-oxazolidinone) were coated onto the surfaces of pieces of polyurethane medical catheters as substrates using procedures discussed in example 21. Analogous unchlorinated samples were also prepared to be used as controls. The samples which were approximately 2 to 3 square millimeters in surface area and 150 micrometers thick were placed in coarse mesh histological specimen bags in a 15 milliliter chamber through which a suspension of Pseudomonas aeruginosa ($10^5$ CFU per milliliter) was flowed constantly at a rate of approximately 200 milliliters per day for a total of three days. Samples were removed at 24 hour intervals, fixed in 4% glutaraldehyde for 2 hours, dehydrated by exposure to ethanol rinses, coated with gold (20 nanometers) using a Sputter Coater Model SC500, and subjected to analysis using a JEOL Scanning Electron Microscope for comparison of the extent of adherence of the Pseudomonas organisms to the test and control surfaces. At each test period the bacteria were observed to be adherent in increasing numbers to the control sample surfaces, so that by 72 hours there was extensive slime formation over the entire surface as a homogeneous layer. In contrast, no biofilm formation occurred on the chlorinated test sample at any observation point. A few colonies of Pseudomonas were adherent on the 4e surfaces after 72 hours, but the 3 g surface was almost entirely free of bacteria at this sampling time. It may be concluded from these data that surfaces treated with certain N-halamine polymers can effectively inhibit biofilm formation by Pseudomonas aeruginosa (an important biofilm-forming contaminant in aqueous flow systems in industry and medicine) for up to 72 hours.

Example 26

Use of Grafted Copolymer 4c as a Preservative Biocide in Emulsions

Samples of poly-vinyl alcohol-g-4-(acryloxymethyl)-4-ethyl-2-oxazolidinone which is the precursor for the chlorinated copolymer 4c were tested for efficacy at preventing biofouling in poly-vinyl alcohol, which is used as an emulsifier in various emulsions, paints, and coatings. 5.0 grams of a 10% aqueous poly-vinyl alcohol solution and 5.0 grams poly-vinyl alcohol-g-4-(acryloxymethyl)-4-ethyl-2-oxazolidinone were spiked with 0.5 milliliters of a diluted aqueous solution of sodium hypochlorite and were loosely covered and allowed to stand at room temperature. The samples were inspected periodically to determine if any viable bacteria were apparent. It was found that after three months the ungrafted poly-vinyl alcohol had severe biofouling, while the grafted copolymer had none; in fact, the grafted poly-vinyl alcohol showed no biofouling for up to six months at which time the experiment was concluded. Therefore polymer 4c should be effective as a preservative at low concentration for emulsions which do not contain reducing agents such as bisulfites, thiosulfates, etc.

Example 27

Preparation of 3-(acryloxymethyl)-5,5-dimethylhydantoin and its 1-chloro Derivative To a three-neck round bottom flask equipped with a condenser, an addition funnel and a gas inlet, were added 100 milliliters of chloroform, 15.8 grams (0.10 mole) 3-hydroxymethyl-5,5-dimethylhydantoin (TCI Co., recrystallized from ethyl acetate), and 10.1 grams (0.101 mole) freshly distilled triethylamine. To the mixture in an ice bath, 10.08 grams (0.101 mole) acryloyl chloride in 30 milliliters chloroform were added dropwise while the reaction mixture was held under $N_2$ atmosphere. After addition in about 30 minutes, the ice bath was removed, and the mixture was stirred at room temperature for 3 hours. The solvent was removed under reduced pressure, and 100 ml ethyl acetate were added to the residue with stirring. The white solid was filtered off, and the ethyl acetate solution was washed with 0.02 N HCl solution, 10% $NaHCO_3$ solution, saturated NaCl solution, and then dried over anhydrous $Na_2SO_4$. The solvent was removed under reduced pressure to give 19.05 grams (90% of the yield theoretically expected) 3-acryloxymethyl-5,5-dimethylhydantoin as a clear oil. The product exhibited the following spectral data: $^1$H NMR (DMSO-$d_6$) *1.31(s, 6H), 5.43(s, 2H), 5.95–6.41(m, 3H), 8.61(s, 1H); $^{13}$C NMR (DMSO-$d_6$) *24.5, 58.0, 61.6, 127.4, 132.9, 153.5, 164.4, 176.6; IR (NaCl) 3341, 2982, 1738, 1456, 1250, 1163 $cm^{-1}$; MS m/z 212.

1.05 grams (0.005 mole) of 3-acryloxymethyl-5,5-dimethylhydantoin prepared as described above, 1.10 grams (0.01 mole) tertiary butyl hypochlorite, and 10 milliliters methylene chloride were added to a round bottom flask and sealed. The solution was stirred at room temperature for 30 minutes and the solvent removed under reduced pressure. 1.23 grams (100% of that theoretically expected) 1-chloro-3-(acryloxymethyl)-5,5-dimethylhydantoin was obtained as a yellow clear oil. The product had the following spectral data: $^1$H NMR (CDCl$_3$) *1.49 (s, 6H), 5.60 (s, 2H), 5.90–6.50 (m, 3H); $^{13}$C NMR(CDCl$_2$) *24.7, 59.0, 61.7, 127.3, 132.2, 154.6, 164.8, 176.4; IR (NaCl) 3347, 2978, 1751, 1416, 1173 $cm^{-1}$.

Example 28

Preparation of 3-(2'-methylacryloxymethyl)-5,5-dimethylhydantoin 15.80 grams (0.10 mole) 3-hydroxymethyl-5,5-dimethylhydantoin, 100 milliliters of chloroform, and 10.1 grams (0.101 mole) freshly distilled triethylamine were mixed in a three-neck round bottom flask equipped with a condenser, an addition funnel and a nitrogen inlet. To the mixture in an ice bath, 11.50 grams (0.101 mole) 2-methylacryloyl chloride in 30 milliliters chloroform were added dropwise while the reaction mixture was held under $N_2$ atmosphere. After addition in about 30 minutes, the ice bath was removed, and the mixture was stirred at room temperature for 3 hours. The solvent was removed under reduced pressure, and 100 ml ethyl acetate were added to the residue with vigorous stirring. The solid was filtered off, and the ethyl acetate solution was washed with 0.02 N HCl solution, 10% $NaHCO_3$ solution, saturated NaCl solution, and then dried over anhydrous $Na_2SO_4$. The solvent was removed under reduced pressure to give 20.52 grams (91% of that theoretically expected) of pure product as a clear oil. The product exhibited the following spectral data: $^1$H NMR (DMSO-$d_6$) *1.26(s, 6H), 1.93(s, 3H), 5.60(s, 2H), 5.64(s, 1H), 6.12(s, 1H), 7.06(s, 1H); $^{13}$C NMR (DMSO-$d_6$) *17.7, 24.5, 56.2, 62.0, 126.8, 135.3, 153.7, 172.1, 176.7; IR (NaCl) 3351, 2985, 1734, 1456, 1149 $cm^{-1}$; MS m/z 226.

Example 29

Preparation of poly-3-(acryloxymethyl)-5,5-dimethylhydantoin 2.12 grams (0.01 mole) 3-(acryloxymethyl)-5,5-dimethylhydantoin, as prepared in example 27, 0.01 gram ($6 \times 10^{-5}$ mole) 2,2'-azobisisobutyronitrile, and 10 milliliters anhydrous N,N-dimethylformamide were placed in a two-neck round bottom flask. The reaction mixture was purged with nitrogen for 15 minutes, and the flask was sealed and heated to 60° C. for 10 hours with stirring. The solution was cooled to room temperature and the polymer precipitated in 250 milliliters water. The polymer was filtered off, redissolved in N,N-dimethylformamide, and reprecipitated in water two more times. The resulting solid was filtered and dried in a vacuum oven to give 2.02 grams (95% of the yield theoretically expected) pure product as a white solid. The product, poly-3-(acryloxymethyl)-5,5-dimethylhydantoin, exhibited the following spectral data: $^1$H NMR (DMSO-$d_6$) *1.31, 2.22, 5.35, 8.40; $^{13}$C NMR (DMSO-$d_6$) *24.4, 35.8, 56.1, 57.9, 61.2, 153.5, 172.5, 176.4; IR (KBr) 3341, 2982, 1738, 1456 $cm^{-1}$.

Example 30

Preparation of poly-acrylonitrile-co-1-halo-3-(acryloxymethyl)-5,5-dimethylhydantoin (30-Cl, 30-Br)

1.06 grams (0.005 mole) 3-(acryloxymethyl)-5,5-dimethylhydantoin, as prepared in example 27, 4.24 grams (0.08 mole) acrylonitrile, 0.03 grams ($1.83 \times 10^{-4}$ mole) 2,2'-azobisisobutyronitrile, and 15 milliliters anhydrous N,N-dimethylformamide were placed in a two-neck round bottom flask. The reaction mixture was purged with nitrogen for 15 minutes, and the flask was sealed and heated to 65° C. for 10 hours with stirring. The solution was cooled to room temperature and the polymer precipitated in 250 milliliters water. The polymer was filtered off, redissolved in N,N-dimethylformamide, and reprecipitated in water two more times. The resulting solid was filtered and dried in a vacuum oven to give 4.82 grams (90% of the yield theoretically expected) pure product as a white solid. The product, poly-acrylonitrile-co-3-(acryloxymethyl)-5,5-dimethylhydantoin, exhibited the following spectral data: $^1$H NMR (DMSO-$d_6$) δ1.33, 2.09, 3.14, 3.35, 5.46, 8.60; $^{13}$C NMR (DMSO-$d_6$) δ14.1, 20.7, 25.1, 59.8, 63.8, 115.2, 122.0, 126.7, 149.9, 156.3, 164.2, 170.4, 176.9; IR (KBr) 3377, 2938, 2243, 1777, 1732, 1456 $cm^{-1}$.

1.0 gram poly-acrylonitrile-co-3-(acryloxymethyl)-5,5-dimethylhydantoin, prepared as described above and 50 milliliters 1.0 normal sodium hydroxide were added to an Erlenmeyer flask. The stirred, heterogeneous mixture was cooled in an ice bath until the temperature was 10° C. Chlorine gas (Matheson Gas Co., Montgomeryville, Pa.) was bubbled into the solution slowly so that the temperature did not exceed 15° C. Once the pH of the solution reached 7.0, the chlorine gas flow was stopped, and the mixture was stirred for 30 more minutes. The mixture was allowed to come to room temperature and was vacuum filtered. The resulting solid was washed with 200 milliliters distilled water and was air dried to give 1.0 gram poly-acrylonitrile-co-1-chloro-3-(acryloxymethyl)-5,5-dimethylhydantoin (30-Cl) as a white solid. The product exhibited the following spectral data: IR (KBr) 2938, 2244, 1788, 1734, 1456 cm$^{-1}$.

1.0 gram poly-acrylonitrile-co-3-(acryloxymethyl)-5,5-dimethylhydantoin, prepared as described above, and 50 milliliters 1.0 normal sodium hypobromite were stirred at room temperature for 30 minutes in a sealed flask. The solution was then filtered and the solid washed with 200 milliliters distilled water and dried to give 1.0 gram poly-acrylonitrile-co-1-bromo-3-(acryloxymethyl)-5,5-dimethylhydantoin (30-Br) as a pale yellow solid. The product exhibited the following spectral data: IR (KBr) 2937, 2244, 1786, 1733, 1456 cm$^{-1}$.

Example 31

Preparation of Poly-methyl methacrylate-co-1-chloro-3-(acryloxymethyl)-5,5-dimethylhydantoin (31-Cl)

A copolymerization was performed with 1.0 gram (4.7×10$^{-3}$ mole) of 3-(acryloxymethyl)-5,5-dimethylhydantoin and 4.0 grams (0.04 mole) of methyl methacrylate using the procedure employed which was identical to that discussed in example 30. The yield of poly-methyl methacrylate-co-3-(acryloxymethyl)-5,5-dimethylhydantoin was 92% of that theoretically expected. The product exhibited prominent infrared bands in a KBr pellet at 3446, 2952, 1734, 1456, 1149 cm$^{-1}$.

Chlorination of the above sample in the manner analogous to that discussed in example 30 produced poly-methyl methacrylate-co-1-chloro-3-(acryloxymethyl)-5,5-dimethylhydantoin (5-Cl) in 100% yield with prominent infrared bands in a KBr pellet at 2952, 1791, 1734, 1457, 1149 cm$^{-1}$. The bromination can be done in the same manner described in example 30.

Example 32

Preparation of poly-vinyl acetate-co-3-(acryloxymethyl)-5,5-dimethylhydantoin

A copolymerization was performed with 1.0 gram (4.7×10$^{-3}$ mole) of 3-(acryloxymethyl)-5,5-dimethylhydantoin and 4.0 grams (0.046 mole) of vinyl acetate using the procedure employed which was identical to that discussed in example 30. The yield of poly-vinyl acetate-co-3-(acryloxymethyl)-5,5-dimethylhydantoin was 86% of that theoretically expected. The product exhibited prominent infrared bands in a KBr pellet at 3355, 2980, 1740, 1240, 1022 cm$^{-1}$.

Example 33

Preparation of poly-acrylonitrile-co-3-(acryloxymethyl)-5,5-dimethylhydantoin by emulsion polymerization 4.2 grams (0.02 mole) 3-(acryloxymethyl)-5,5-dimethylhydantoin, prepared identically to that discussed in example 27, 10.0 grams (0.190 mole) acrylonitrile, 30 milliliters deionized water, and 0.20 grams (6.94×10$^{-4}$ mole) sodium lauryl sulfate were added to a three-neck round bottom flask equipped with a gas inlet and reflux condenser. The solution was stirred and heated at 60° C. and purged with nitrogen for ten minutes. A solution of 0.025 grams (9.26×10$^{-5}$ mole) potassium persulfate and 1.0 milliliter water was prepared and added in the reaction mixture after the nitrogen purge was completed. The reaction was stirred for eight hours and then cooled to room temperature. Any precipitated polymer was allowed to settle, and the latex was decanted off. The polymer can be isolated by pouring the latex into 150 milliliters of water, then slowly adding salt with stirring to coagulate the emulsion. The polymer was collected by filtration, washed with water, and dried at room temperature. The product poly-acrylonitrile-co-3-(acryloxymethyl)-5,5-dimethylhydantoin was produced in 91% yield with infrared bands in a KBr pellet at 3375, 2938, 2243, 1732, 1456 cm$^{-1}$.

Example 34

Preparation of poly-ethyl acrylate-co-styrene-co-3-(acryloxymethyl)-5,5-dimethylhydantoin latex 4.2 grams (0.02 mole) 3-(acryloxymethyl)-5,5-dimethylhydantoin, prepared identically to that discussed in example 27, 8.0 grams (0.08 mole) ethyl acrylate, 2.1 grams (0.02 mole) styrene, 30 milliliters deionized water, and 0.20 grams (6.94×10$^{-4}$ mole) sodium lauryl sulfate were added to a three-neck round bottom flask equipped with a gas inlet and reflux condenser. The solution was stirred and heated at 60° C. and purged with nitrogen for ten minutes. A solution of 0.025 grams (9.26×10$^{-5}$ mole) potassium persulfate and 1.0 milliliter water was prepared and added in the reaction mixture after the nitrogen purge was completed. The reaction was stirred for eight hours and then cooled to room temperature. Any precipitated polymer was allowed to settle, and the latex was decanted off. The polymer can be isolated by pouring the latex into 150 milliliters of water, then slowly adding salt with stirring to coagulate the emulsion. The polymer was collected by filtration, washed with water, and dried at room temperature. The product poly-ethyl acrylate-co-styrene-co-3-(acryloxymethyl)-5,5-dimethylhydantoin was produced in 96% yield with infrared bands in a KBr pellet at 3380, 3058, 2924, 1773, 1738, 1453 cm$^{-1}$.

Example 35

Preparation of poly-vinyl acetate-co-methyl methacrylate-co-3-(acryloxymethyl)-5,5-dimethylhydantoin latex An emulsion copolymerization was performed with vinyl acetate (8.6 grams, 0.10 mole) and methyl methacrylate (4.0 grams, 0.04 mole) and 3-(acryloxymethyl)-5,5-dimethylhydantoin (4.2 grams, 0.02 mole) using the procedure employed which was identical to that discussed in example 34. The yield of poly-vinyl acetate-co-methyl methacrylate-co-3-(acryloxymethyl)-5,5-dimethylhydantoin was 93% of that theoretically expected. The product had infrared bands in a KBr pellet at 3365, 2980, 1740, 1240 cm$^{-1}$.

Example 36

Preparation of poly-vinyl acetate-co-butyl acrylate-co-3-(acryloxymethyl)-5,5-dimethylhydantoin latex An emulsion copolymerization was performed with vinyl acetate (8.6 grams, 0.10 mole) and butyl acrylate (2.6 grams, 0.02 mole) and 3-(acryloxymethyl)-5,5-dimethylhydantoin (4.2 grams, 0.02 mole) using the procedure employed which was identical to that discussed in example 34. The yield of poly-vinyl acetate-co-butyl acrylate-co-3-(acryloxymethyl)-5,5-dimethylhydantoin was 91% of that theoretically expected. The product had infrared bands in a KBr pellet at 3370, 2975, 1734, 1457 $cm^{-1}$.

Example 37

Preparation of poly-acrylonitrile-g-3-(acryloxymethyl)-5,5-dimethylhydantoin 2.1 grams (0.01 mole) 3-(acryloxymethyl)-5,5-dimethylhydantoin, prepared identically to that discussed in example 27, 10 grams poly-acrylonitrile latex which was prepared from acrylonitrile using the method described by Hayes, R. A., *J. Polymer Sci.* 11:531 (1967), and 20 milliliters of water, were added to a three-neck round bottom flask. The reagents were purged with nitrogen for fifteen minutes; the flask was then sealed and heated to 60° C. with stirring. Once the internal temperature reached 60° C., 0.05 grams ($1.9 \times 10^{-4}$ mole) sodium persulfate dissolved in 1.0 milliliter water was added into the reaction mixture. The reaction mixture was heated and stirred for twelve hours, then cooled to room temperature. The solution was poured into 150 milliliters of a saturated sodium chloride solution, and the solid was collected by filtration and extracted with 200 milliliters boiling 50/50 DMF/water. The resulting solid was refiltered and air dried to give 5.0 grams product, poly-acrylonitrile-g-3-(acryloxymethyl)-5,5-dimethylhydantoin which exhibited prominent infrared bands in a KBr pellet at 3377, 2938, 2243, 1730 $cm^{-1}$.

Example 38

Preparation of poly-vinyl alcohol-g-3-(acryloxymethyl)-5,5-dimethylhydantoin 5.0 grams poly-vinyl alcohol (molecular weight 85000–146000) dissolved in 30 milliliters deionized water and 2.10 grams (0.01 mole) 3-(acryloxymethyl)-5,5-dimethylhydantoin, prepared identically to that discussed in example 27, were added to a three-neck round bottom flask. The mixture was purged with nitrogen for fifteen minutes; the flask was then sealed and heated to 60° C. with stirring. Once the internal temperature reached 60° C., 0.05 grams ($1.9 \times 10^{-4}$ mole) sodium persulfate dissolved in 1.0 milliliter water was added into the reaction mixture. The reaction mixture was heated and stirred for twelve hours to give poly-vinyl alcohol-g-3-(acryloxymethyl)-5,5-dimethylhydantoin latex.

Example 39

Preparation of cellulose-g-3-(acryloxymethyl)-5,5-dimethylhydantoin 1.00 gram cellulose and 50.0 milliliters 0.05 normal nitric acid were placed in an Erlenmeyer flask and stirred for 30 minutes at 30° C. under nitrogen. 1.06 grams (0.005 mole) 3-(acryloxymethyl)-5,5-dimethylhydantoin, prepared identically to that discussed in example 27, were added, and the mixture was stirred for another 15 minutes; then 0.11 grams ($2.0 \times 10^{-4}$ mole) ammonium ceric nitrate was added to the reaction. A continuous supply of nitrogen was maintained throughout the reaction time of 30 minutes, at which time the polymerization was complete, and the product was filtered off. The solid was washed with distilled water and then acetone and dried in an oven to give 1.09 grams of cellulose-g-3-(acryloxymethyl)-5,5-dimethylhydantoin. The percentage add-on is 9%.

Example 40

Efficacies of the Poly N-halamine Compounds against *Staphylococcus aureus*

Solid samples of the polymeric N-halamine compounds described in examples 30 and 31 were packed into glass Pasteur pipettes (5.75 inches long, 0.25 inches inside diameter) at a length of 1.0 inch. The samples were washed with pH 7.0 aqueous solution and then $10^6$ CFU per milliliter of *Staphylococcus aureus* (ATCC 6538) were added to the pipette, and the inoculum was allowed to pass through the packed column using gravity feed. The effluent from each sample was collected, and a 25.0 µL aliquot was quenched with an equal volume of 0.02 N sodium thiosulfate. A 25.0 µL sample of the mixture was plated on nutrient agar. The bulk bacteria solution was recycled through the columns. This procedure was repeated typically 6 times which allowed for an assessment of biocidal contact time. The plated samples were incubated at 37° C. for 48 hours and then examined for viable growth. Control samples consisted of plating aliquots of the bacterial suspension before passing through the biocidal polymer columns, and of passing the bacteria through columns containing unchlorinated precursor polymer samples. In all cases the two types of control experiments yielded plates which contained confluent growth too numerous to count indicating that the bacterial samples were viable and that the organisms were not simply eliminated by filtration upon passing through the samples. Results are tabulated in Table VI. They demonstrate that the materials were biocidal.

TABLE VI

Biocidal Effects of the N-halamine Polymers

| Polymer[a] | Mesh Size | Column Length (Inches) | Age (Days)[b] | Contact time for 6-log Inactivation of S. aureus (min) |
|---|---|---|---|---|
| 30-Cl | 30-60 | 1.0 | 1 | <0.9 |
| 30-Cl | 30-60 | 1.0 | 60 | 1.5–2.3 |
| 30-Br | 30-60 | 1.0 | 1 | <0.9 |
| 31-Cl | 30-60 | 1.0 | 1 | 1.0–1.3 |
| 31-Cl | 30-60 | 1.0 | 60 | 1.8–2.4 |

[a]30-Cl = poly-acrylonitrile-co-1-chloro-3-(acryloxymethyl)-5,5-dimethylhydantoin
30-Br = poly-acrylonitrile-co-1-bromo-3-(acryloxymethyl)-5,5-dimethylhydantoin
31-Cl = poly-methyl methacrylate-co-1-chloro-3-(acryloxymethyl)-5,5-dimethylhydantoin
[b]Time in days elapsing between sample synthesis and biocidal test run with storage at room temperature.

Example 41

Preparation of Films and Surface Coatings

Unchlorinated poly N-halamine compounds described in examples 32–38 were cast into thin films on various surfaces and then chlorinated so as to determine the biocidal efficacy of these disinfectant surfaces. The general method of film forming is as follows. 1 gram of the unchlorinated polymer was dissolved in about 10 milliliters of an appropriate solvent. The solution was added to cover the pre-cleaned surface of substrate without running over the sides. The solvent was evaporated in air, and the substrate was heated in an oven until the solvent was completely removed and dry coating resulted. In all cases, the coating was clear, tough, resistant to abrasion, and had good adherence to the substrate. Once coated, the surface was chlorinated with a diluted solution of sodium hypochlorite (3000 ppm free chlorine) by soaking in the aqueous solution for 1 hour. The surface was then removed, washed with chlorine-demand-free water, and air dried at room temperature to ensure all residual sodium hypochlorite was removed.

For the case in which an emulsion or latex was used, the emulsified solution was added directly to the substrate and heated in the oven to remove the solvent, water, as well as coalesce the polymer particles to form the coating. The chlorination of the coating was done in the same manner as described above.

Example 42

Efficacies of Poly N-halamine Surfaces Against Staphylococcus aureus

The surfaces to be tested for biocidal activity against *S. aureus* (ATCC 6538) were applied to a square microscope glass slide. The surfaces were chlorinated in the same manner as mentioned in example 41. 50 microliters of a $10^6$ CFU solution *S. aureus* were placed on the surface, and a 25 microliters aliquot was removed at a predetermined time, and the active halogen was quenched by sterile 0.02 normal sodium thiosulfate. The mixture was then applied to the dried surface of a Petri dish containing nutrient agar. After incubation at 37° C. for 48 hours, the bacteria were counted. Control samples containing no disinfectant, or in some cases, unchlorinated precursor surfaces, were handled in the same manner. In all cases the two types of control experiments yielded plates which contained confluent growth too numerous to count indicating that the bacteria samples were viable.

The data in Table VII demonstrate that all of the N-halamine biocidal polymers tested effectively deactivated *S. aureus* on a glass substrate.

TABLE VII

Biocidal Effects of the N-halamine Surfaces

| Polymer[a] | Chlorination Time (min) | Age (days)[b] | Contact Time (min) | the Number of log Inactivation of *S. aureus* |
|---|---|---|---|---|
| 32 | 30 | 1 | 30 | >4.1 |
| 33 | 30 | 1 | 30 | >4.1 |
| 34 | 30 | 1 | 30 | >4.1 |
| 35 | 30 | 1 | 30 | >4.1 |
| 36 | 30 | 1 | 30 | >4.1 |
| 37 | 30 | 1 | 30 | >4.1 |
| 38 | 30 | 1 | 30 | >4.1 |

[a]32 = poly-vinyl acetate-co-3-(acryloxymethyl)-5, 5-dimethylhydantoin
33 = poly-acrylonitrile-co-3-(acryloxymethyl)-5, 5-dimethylhydantoin
34 = poly-ethyl acrylate-co-styrene-co-3-(acryloxymethyl)-5, 5-dimethylhydantoin latex
35 = poly-vinyl acetate-co-methyl methacrylate-co-3-(acryloxymethyl)-5, 5-dimethylhydantoin latex
36 = poly-vinyl acetate-co-butyl acrylate-co-3-(acryloxymethyl)-5, 5-dimethylhydantoin latex
37 = poly-acrylonitrile-g-1-chloro-3-(acryloxymethyl)-5, 5-dimethylhydantoin
38 = poly-vinyl alcohol-g-1-chloro-3-(acryloxymethyl)-5, 5-dimethylhydantoin
[b]Time in days elapsing between sample synthesis and biocidal test run with storage at room temperature.

Example 43

Zone of Inhibition Study of Sample 39

The sample 39, cellulose-g-3-(acryloxymethyl)-5,5-dimethylhydantoin (1 cm×1 cm), was chlorinated by soaking in 2% NaOCl aqueous solution for one hour, washed thoroughly with chlorine-demand-free water, and then air dried. A piece of 1 cm square of this sample was placed on a Tryptic Soy agar plate which was inoculated with *Staphylococcus aureus* (ATCC 6538). The plate was incubated for 24 hours at 37° C. The zone of inhibition was distinct, and it was measured to be 1.2 mm from the edge of the sample to the viable bacteria.

Example 44

Preparation of Thermosetting Coatings

A 250 mL three-neck flask was equipped with condenser, dropping funnel, nitrogen inlet, and stirrer. It was flushed with nitrogen, and 40 mL methyl ethyl ketone were added. A batch containing 3.50 g ($3.50 \times 10^{-2}$ mole) methyl methacrylate, 1.72 g ($1.48 \times 10^{-2}$ mole) 2-hydroxyethyl acrylate, 6.64 g ($3.10 \times 10^{-2}$ mole) 3-(acryloxymethyl)-5,5-dimethylhydantoin (prepared as described in Example 27), and 0.20 g ($1.2 \times 10^{-3}$ mole) 2,2'-azobisisobutyronitrile was added to the dropping funnel. The methyl ethyl ketone was brought to reflux under a light stream of nitrogen, and the monomer-initiator batch was then added at a constant rate over a period of 30 minutes. After the addition, refluxing was continued for 3 hours. The solution was then allowed to cool and weighed (44.14 g). A portion of the copolymer was isolated by precipitation into ethanol, followed by filtration, ethanol washing, and air drying. The copolymer, poly-methyl methacrylate-co-3-(acryloxymethyl)-5,5-dimethylhydantoin-co-2-hydroxyethyl acrylate, exhibited the following spectra: $^1$H NMR (DMSO-$d_6$) δ0.74–0.99, 1.05, 1.31, 3.29–3.55, 4.36, 5.33, 8.49; $^{13}$C NMR (DMSO-$d_6$) δ18.5, 24.4, 44.4, 51.6, 56.0, 57.9, 58.7, 61.1, 65.7, 153.4, 175.1, 176.3.

To a 10.0 g solution of the copolymer prepared as above, 0.42 g ($1.678 \times 10^{-3}$ mole) 4,4'-methylenebis(phenyl isocyanate) and 0.10 g ($7.41 \times 10^{-4}$ mole) dimethylbenzylamine were added. The mixture was stirred vigorously for five minutes and then coated onto a glass slide. The sample was allowed to dry in air and then heated in an oven at 90° C. for 2 hours. A clear, strong thermosetting coating resulted.

To a 10.0 g solution of the copolymer prepared as above, 0.28 g ($1.678 \times 10^{-3}$ mole) 1,6-diisocyanatohexane and 0.10 g ($7.41 \times 10^{-4}$ mole) dimethylbenzylamine were added. The mixture was stirred vigorously for five minutes and then coated onto a glass slide. The sample was allowed to dry in air and then heated in an oven at 90° C. for 2 hours. A clear, strong thermosetting coating resulted from this treatment also.

As discussed above, a 250 mL three-neck flask was equipped with condenser, dropping funnel, nitrogen inlet, and stirrer. It was flushed with nitrogen, and 40 mL methyl ethyl ketone were added. A batch containing 3.60 g ($3.60 \times 10^{-2}$ mole) methyl methacrylate, 0.72 g ($1.00 \times 10^{-2}$ mole) acrylic acid, 6.12 g ($2.89 \times 10^{-2}$ mole) 3-(acryloxymethyl)-5,5-dimethylhydantoin, and 0.20 g ($1.2 \times 10^{-3}$ mole) 2,2'-azobisisobutyronitrile was added to the dropping funnel. The methyl ethyl ketone was brought to reflux under a light stream of nitrogen, and the monomer-initiator batch was then added at a constant rate over a period of 30 minutes. After the addition, refluxing was continued for another 3 hours. The solution was then allowed to cool and weighed (41.66 g). A portion of the copolymer was isolated by precipitation into ethanol, followed by filtration, ethanol washing, and air drying. The copolymer, poly-methyl methacrylate-co-3-(acryloxymethyl)- 5,5-dimethylhydantoin-co-acrylic acid, exhibited following spectra: $^1$H NMR (DMSO-d$_6$) δ0.74–1.05, 1.30, 1.58–2.20, 3.34–3.55, 4.36, 5.33, 8.51, 12.31; $^{13}$C NMR (DMSO-d$_6$) δ7.7, 17.9, 18.5, 24.4, 44.3, 51.6, 56.1, 57.9, 61.1, 153.4, 175.8, 176.3.

To a 10.0 g solution of copolymer prepared as above, 0.30 g (1.199×10$^{-3}$ mole) 4,4'-methylenebis(phenyl isocyanate) and 0.10 g (7.41×10$^{-4}$ mole) dimethylbenzylamine were added. The mixture was stirred vigorously for five minutes and then coated onto a glass slide. The sample was allowed to dry in air and then heated in an oven at 90° C. for 2 hours. A clear, strong thermosetting coating resulted.

To a 10.0 g solution of copolymer prepared as above, 0.20 g (1.199×10$^{-3}$ mole) 1,6-diisocyanatohexane and 0.10 g (7.41×10$^{-4}$ mole) dimethylbenzylamine were added. The mixture was stirred vigorously for five minutes and then coated onto a glass slide. The sample was allowed to dry in air and then heated in an oven at 90° C. for 2 hours. A clear, strong thermosetting coating resulted.

All of the thermosetting coatings were activated for biocidal testing by soaking the coated slides in 5% sodium hypochlorite solution.

Example 45

Preparation of Polyurethane Materials

The monomer 4,4-dihydroxymethyl-2-oxazolidinone was synthesized by a procedure similar to that reported by Horn, et al. in U.S. Pat. No. 3,133,932, but with some modifications. To a 250 milliliter round-bottom flask were added 12.1 g (0.10 mole) trishydroxymethylaminomethane, 6.0 g (0.10 mole) urea, and 50 milliliters N,N-dimethylformamide. The mixture was then refluxed at 160° C. for 6 hours. The N,N-dimethylformamide solvent was then removed by distillation, and 100 milliliters of ethyl acetate were added to the residue with stirring. The solid product was isolated by vacuum filtration and recrystallized from acetone. The yield was 10.3 g (70%); the mp was 107–108.5° C.

0.94 g (5.48×10$^{-3}$ mole) 1,6-diisocyanatohexane, 0.81 g (5.48×10$^{-3}$ mole) 4,4-dihydroxymethyl-2-oxazolidinone, 10 mL anhydrous N,N-dimethylformamide, and 0.20 g (1.48×10$^{-3}$ mole) N,N-dimethylbenzylamine were mixed in a 50 mL round-bottom flask. The mixture was heated in an oil bath at 90° C. under reflux for 5 hours. After cooling to room temperature, a portion of the solution was coated onto a glass slide. The solvent was evaporated in air first and then in a vacuum oven at 90° C., and a clear, strong coating resulted. The coating was activated for biocidal testing by soaking the slide in 5% sodium hypochlorite solution.

0.735 g (5.0×10$^{-3}$ mole) 4,4-dihydroxymethyl-2-oxazolidinone, 1.714 g (1.0×10$^{-2}$ mole) 1,6-diisocyanatohexane, 10 mL anhydrous N,N-dimethylformamide, and 0.20 g (1.48×10$^{-3}$ mole) N,N-dimethylbenzylamine were mixed in a three-neck 50 mL round bottom flask. The mixture was heated in an oil bath at 90° C. under reflux for 1 hour, and then 0.45 g (5.0×10$^{-3}$ mole) 1,4-butanediol was added through an addition funnel. The reaction was stirred for another 5 hours under reflux and then cooled to room temperature. A portion of the solution was coated onto a glass slide. The solvent was evaporated in air first and then in a vacuum oven at 90° C., and a clear, strong coating resulted. The coating was activated by soaking in 5% sodium hypochlorite solution.

Example 46

Efficacies of Poly N-halamine Coatings Against *Staphylococcus aureus*

The surface bactericidal tests were performed on the theromosetting coatings and polyurethane coatings against *S. aureus* in as discussed in Example 42. The results are tabulated in Table VIII.

TABLE VIII

Biocidal Efficacies of the N-halamine Coatings

| Coating[a] | Chlorination Time (min) | Age (days)[b] | Contact Time (min) | Log Reduction S. aureus |
|---|---|---|---|---|
| 44a | 30 | 1 | 30 | 3.7 |
| 44b | 30 | 1 | 30 | 3.5 |
| 44c | 30 | 1 | 30 | 2.0 |
| 44d | 30 | 1 | 30 | 2.1 |
| 45a | 60 | 1 | 60 | >4.6 |
| 45b | 60 | 1 | 60 | >4.6 |
| 45a | 60 | 7 | 60 | >4.6 |
| 45b | 60 | 7 | 60 | >4.6 |

[a]44a = Poly-methyl methacrylate-co-3-(acryloxymethyl)-5, 5-dimethylhydantoin-co-2-hydroxyethyl acrylate, crosslinked by reaction with 4, 4'-methylenebis(phenyl isocyanate).
44b = Poly-methyl methacrylate-co-3-(acryloxymethyl)-5, 5-dimethylhydantoin-co-2-hydroxyethyl acrylate, crosslinked by reaction with 1, 6-diisocyanatohexane.
44c = Poly-methyl methacrylate-co-3-(acryloxymethyl)-5, 5-dimethylhydantoin-co-acrylic acid, crosslinked by reaction with 4, 4'-methylenebis(phenyl isocyanate).
44d = Poly-methyl methacrylate-co-3-(acryloxymethyl)-5, 5-dimethylhydantoin-co-acrylic acid, crosslinked by reaction with 1, 6-diisocyanatohexane.
45a = Polyurethane prepared from 4, 4-dihydroxymethyl-2-oxazolidinone and 1, 6-diisocyanatohexane.
45b = Polyurethane prepared from 1, 4-butanediol, 4, 4-dihydroxymethyl-2-oxazolidinone and 1, 6-diisocyanatohexane.
[b]Time in days elapsing between sample synthesis and biocidal test run with storage at room temperature.

As can be seen, the coatings were bactericidal against *S. Aureus*.

Example 47

Efficacies of Poly N-halamine Coatings Against *E. coli*

The surface bacterial tests were performed on the theromosetting coatings and polyurethane coatings against *E. coli* using the procedure discussed in Example 42. The results are tabulated in Table IX.

TABLE IX

Biocidal Efficacies of the N-halamine Coatings

| Coating[a] | Chlorination Time (min) | Age (days)[b] | Contact Time (min) | Log Reduction E. coli |
|---|---|---|---|---|
| 44a | 30 | 1 | 45 | 3.9 |
| 44c | 30 | 1 | 45 | 1.5 |
| 45a | 60 | 1 | 60 | >4.7 |
| 45b | 60 | 1 | 30 | >4.8 |

TABLE IX-continued

Biocidal Efficacies of the N-halamine Coatings

| Coating[a] | Chlorination Time (min) | Age (days)[b] | Contact Time (min) | Log Reduction E. coli |
|---|---|---|---|---|

[a]44a = Poly-methyl methacrylate-co-3-(acryloxymethyl)-5,
5-dimethylhydantoin-co-2-hydroxyethyl acrylate, crosslinked by reaction with 4, 4'-methylenebis (phenyl isocyanate).
44c = Poly-methyl methacrylate-co-3-(acryloxymethyl)-5,
5-dimethylhydantoin-co-acrylic acid, crosslinked by reaction with 4, 4'-methylenebis (phenyl isocyanate).
45a = Polyurethane prepared from 4, 4-dihydroxymethyl-2-oxazolidinone and 1, 6-diisocyanatohexane.
45b = Polyurethane prepared from 1, 4-butanediol, 4, 4-dihydroxymethyl-2-oxazolidinone and 1, 6-diisocyanatohexane.
[b]Time in days elapsing between sample synthesis and biocidal test run with storage at room temperature.

As can be seen, the coatings were bactericidal against *E. Coli*.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A monomer having structure IV:

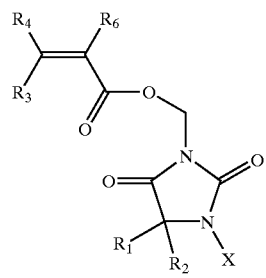

wherein X is hydrogen, chlorine, or bromine; $R_1$ and $R_2$ are independently hydrogen, $C_1$–$C_4$ alkyl, benzyl, alkyl-substituted benzyl, phenyl, or alkyl-substituted phenyl; and $R_3$, $R_4$, and $R_5$ are independently hydrogen, $C_1$–$C_4$ alkyl, benzyl, alkyl-substituted benzyl, phenyl, or alkyl-substituted phenyl.

2. The monomer of claim 1, wherein $R_1$ and $R_2$ are methyl; and $R_3$, $R_4$, and $R_5$ are independently hydrogen or methyl.

3. The monomer of claim 2, wherein the monomer is 3-(acryloxymethyl)-5,5-dimethylhydantoin.

* * * * *

UNITED STATES PATENT AND TRADEMARK OFFICE
CERTIFICATE OF CORRECTION

PATENT NO.    : 6,469,177 B1                                          Page 1 of 1
DATED         : October 22, 2002
INVENTOR(S)   : S.D. Worley et al.

It is certified that error appears in the above-identified patent and that said Letters Patent is hereby corrected as shown below:

<u>Title page,</u>
Item [56], References Cited, U.S. PATENT DOCUMENTS, "Worley et al." should read -- Worley --;
Please insert in appropriate order:
-- 5,057,612     10/1991        Worley et al.
3,374,242        3/1968         Kelley et al.
5,902,818        5/1999         Worley et al. --
OTHER PUBLICATIONS, "Noc. 7," should read -- Nov. 7, --; and
"*Ing.*" should read -- *Ind.* --.

<u>Column 38,</u>
Line 2, after "structure IV:" insert a new paragraph -- STRUCTURE IV: --

Signed and Sealed this

Eighteenth Day of November, 2003

JAMES E. ROGAN
*Director of the United States Patent and Trademark Office*